United States Patent
Pesaro et al.

(10) Patent No.: US 10,638,755 B2
(45) Date of Patent: May 5, 2020

(54) ANTIMICROBIAL COMPOSITIONS

(71) Applicant: Symrise AG, Holzminden (DE)

(72) Inventors: Manuel Pesaro, Holzminden (DE);
Bernd Hölscher, Halle (DE); Gerhard Schmaus, Höxter (DE); Antje Köhler, Holzminden (DE)

(73) Assignee: Symrise AG, Holzminden (DE)

( * ) Notice: Subject to any disclaimer, the term of this patent is extended or adjusted under 35 U.S.C. 154(b) by 79 days.

(21) Appl. No.: 14/773,071

(22) PCT Filed: Mar. 6, 2014

(86) PCT No.: PCT/EP2014/054378
§ 371 (c)(1),
(2) Date: Sep. 4, 2015

(87) PCT Pub. No.: WO2014/135650
PCT Pub. Date: Sep. 12, 2014

(65) Prior Publication Data
US 2016/0015031 A1    Jan. 21, 2016

(30) Foreign Application Priority Data
Mar. 8, 2013 (EP) .................................... 13158411

(51) Int. Cl.
| | | |
|---|---|---|
| *A01N 35/04* | (2006.01) | |
| *A61K 8/36* | (2006.01) | |
| *A61K 8/35* | (2006.01) | |
| *A61Q 17/00* | (2006.01) | |
| *A01N 31/02* | (2006.01) | |
| *A23L 33/10* | (2016.01) | |
| *A01N 31/14* | (2006.01) | |
| *A23L 3/3463* | (2006.01) | |
| *A61K 8/34* | (2006.01) | |
| *A61Q 15/00* | (2006.01) | |
| *C11D 3/48* | (2006.01) | |

(52) U.S. Cl.
CPC ............ *A01N 35/04* (2013.01); *A01N 31/02* (2013.01); *A01N 31/14* (2013.01); *A23L 3/34635* (2013.01); *A23L 33/127* (2016.08); *A61K 8/34* (2013.01); *A61K 8/345* (2013.01); *A61K 8/35* (2013.01); *A61Q 15/00* (2013.01); *A61Q 17/005* (2013.01); *C11D 3/48* (2013.01); *A23V 2002/00* (2013.01)

(58) Field of Classification Search
CPC ........ A01N 31/02; A01N 31/14; A01N 31/04; A23L 33/127; A23L 3/34635; A23V 2002/00; A61K 8/34; A61K 8/345; A61K 8/35; A61Q 15/00; A61Q 17/005; C11D 3/48

USPC .................................................. 424/65, 66
See application file for complete search history.

(56) References Cited

U.S. PATENT DOCUMENTS

| | | | | |
|---|---|---|---|---|
| 5,466,869 | A | * | 11/1995 | Davenport ............ C07C 249/04 564/265 |
| 5,902,820 | A | * | 5/1999 | Jacquess .............. A01N 43/653 504/156 |
| 6,123,953 | A | * | 9/2000 | Greff ...................... A01N 31/02 424/401 |
| 7,582,681 | B2 | * | 9/2009 | Schmaus ................ A01N 31/02 424/44 |
| 9,585,388 | B2 | * | 3/2017 | Pillai ...................... A01N 31/02 |
| 2007/0054967 | A1 | * | 3/2007 | Schmaus ................ A01N 35/06 514/717 |
| 2008/0254130 | A1 | | 10/2008 | Gupta |
| 2013/0136709 | A1 | * | 5/2013 | Pillai ...................... A01N 31/02 424/65 |

FOREIGN PATENT DOCUMENTS

| | | |
|---|---|---|
| WO | 95/20319 A1 | 8/1995 |
| WO | 2008/071027 A1 | 6/2008 |
| WO | 2010/055474 A2 | 5/2010 |

OTHER PUBLICATIONS

Simonsen et al. (BMC Complementary and alternative Medicine (2006, 6:29, pp. 1-4).*
Vosmanska et al. (Anal Bioanal Chem (2005) 382; 1135-1140).*

* cited by examiner

*Primary Examiner* — Sabiha N Qazi
(74) *Attorney, Agent, or Firm* — Dilworth & Barrese

(57) ABSTRACT

Suggested is a antimicrobial agent An antimicrobial composition comprising (a) at least one acetophenone derivative of formula (I) in which $R_1$ stands for hydrogen or methyl, and $R_2$ stands for hydrogen, hydroxyl or a —$OCH_3$ group, or a cosmetically or pharmaceutically acceptable salt thereof, and (b) at least one second antimicrobial agent.

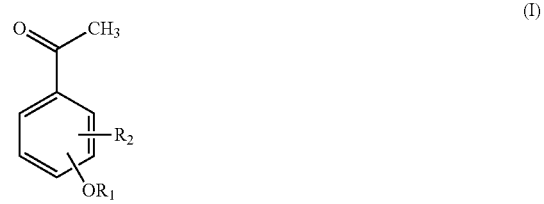

(I)

5 Claims, No Drawings

ANTIMICROBIAL COMPOSITIONS

FIELD OF INVENTION

The present invention belongs to the area of antimicrobial agents for personal care, detergent and nutrition products and refers to new antimicrobial agents and their use in various areas of consumer products.

STATE OF THE ART

In the cosmetics and pharmaceutical and in the foodstuffs industry there is a constant need for agents having antimicrobial properties, in particular for the preservation of products which are otherwise perishable (such as e.g. cosmetics, pharmaceutical products or foodstuffs), but also for direct cosmetic or therapeutic treatment of microorganisms which can have an adverse influence on the human or animal body. Reference may be made by way of example to microorganisms which can cause body odour, acne, mycoses or the like.

In the technical fields referred to a large number of antimicrobial active compounds are indeed already employed, but alternatives nevertheless continue to be sought, in order to be able to perform targeted specific treatments and/or reduce side effects. In this context, however, in the search for alternative agents having an antimicrobial and in particular preserving action it is to be noted that the substances used in the cosmetics, pharmaceutical and/or foodstuffs field must be
- toxicologically acceptable
- readily tolerated by the skin
- stable (in particular in the conventional cosmetic and/or pharmaceutical formulations)
- largely and preferably completely odorless
- inexpensive to prepare (i.e. employing standard processes and/or starting from standard precursors)
- easy to formulate (i.e. preferably liquid) and should not be detrimental to the final product.

Furthermore, they should have antimicrobial activity characteristics, which fulfill the diverse criteria. They should
- provide a broad-spectrum anti-microbial activity against gram positive and gram negative bacteria, yeast and mold
- show a particularly strong activity against the mold *A. brasiliensis*
- be active in different cosmetic formulations at different pH values.

From the state of the art numerous publications are known dealing with various types of products that are active against micro-organisms. For example, Schenk et al. evaluated different fungicides for preservation of moist alfalfa hay (Laboratory evaluation of fungicides for the preservation of moist hay). 4-hydroxyacetophenone was among the compounds tested, but was found to not prevent mold growth and therefore not suitable for hay preservation. Applications in cosmetic formulations are not disclosed (Agronomy Journal, 47, 64-69, 1955).

Zauner et al. published impurities of beet molasses that inhibited the respiration and fermentation of the yeast *Saccharomyces cerevisiae* (Inhibitory activity of impurities of beet molasses and plant protectants on yeast (*Saccharomyces cerevisiae*) respiration and fermentation.) No other microorganisms than *S. cerevisiae* were investigated, particularly, not molds or bacteria. No reference to potential use of the inhibitory substances in the field of cosmetics is given (Brantweinwirtschaft, 119(9), 154-6, 158-60, 163, 1979).

Hirvi et al. investigated the composition of cranberry aroma and found 4-hydroxyaceto-phenone as one constituent. No antimicrobial activity of cranberry aroma or any of its constituents are mentioned (Zeitschrift für Lebensmittel-Untersuchung und-Forschung, 172(5), 365-7, 1981).

Alvarez et al. studied the anti-inflammatory properties of different constituents of the plant *Lampaya hieronymi*. 4-hydroxyacetophenone was one of the active compounds reducing subcuteaneous inflammation when administered intraperitoneally. The agents were not applied topically and no data on antimicrobial activity are disclosed for any of the presented compounds (Il Farmaco, 55, 502-5, 2000).

Schmeda-Hirschmann et al. identified constituents of *Tagetes mendocina* revealing antioxidant activity in a chemical in vitro assay. Among others, 4-hydroxyacetophenone proved to be one of the active constituents. No data on antimicrobial activity and no application for cosmetics are disclosed for any of the presented compounds (Zeitschrift für Naturforschung, 59c, 345-353, 2004).

In this context also reference is made to DE-OS 3629056 (CELAMERCK) discloses the extraction of substance mixtures, including p-hydroxyacetophenone, from the cuticula of spruce needles using apolar solvents. These substance mixtures are claimed to be effective to counteract phytopathogenic fungi, i.e. *Cladosporium cucumerinum* and *Rhizosphaera kalkhoffii*. No other microorganisms, e.g. the non-phytopathogenic yeast *C. albicans* or bacteria are included. Furthermore, no specific application, such as product preservation of cosmetic formulations is mentioned.

WO 1995 020319 A1 (BUCKMAN) covers halogenated acetophenonderivatives useful against bacteriae and fungi. The compositions need to include organic acids, esters or salts.

US 2008/0254130 AA (BIODERM RESEARCH) discloses a topical method of treatment of dysfunction of certain dermal enzymes and the treatment of skin condition or disorder caused by said dysfunction. No antimicrobial activity of the different acetophenone derivatives is described.

WO 2010 055474 A2 (ARIEL UNIV) refers to antimicrobial compositions, comprising aminovinylketones and specific acetophenonderivatives use ful aus medicaments against microbial infections.

JP 07 206645 A (POLA) discloses acetophenone derivatives as hair growth agents. No antimicrobial activity of the different acetophenone derivatives is described.

The search for suitable (active) substances, which have one or more of the properties mentioned to an adequate extent is made difficult for the person skilled in the art in that there is no clear dependency between the chemical structure of a substance on the one hand and its biological activity against certain microorganisms (bacteria, yeast, fungi, small eukaryotes) on the other hand. This makes testing of substances in laboratory experiments inevitable. In addition, the antimicrobial performance in cosmetic formulation cannot be derived from standard anti-microbial screening tests, such as growth inhibition experiments as described in e.g. DIN 58940 or ISO 20776. Many antimicrobial substances characterized by low minimum inhibitory concentrations (MICs) fail to perform in more advanced and applied assays. For product preservation, the highly laborious and time-consuming "challenge test" according to ISO 11930, European Pharmacopoeia 7-5.1.3, or United States Pharmacopoeia 35 has to be used. Furthermore, there is no predictable connection between the chemical structure and other physico-chemical parameters relevant to the field of cosmetics, i.e. the toxicological acceptability, the skin tolerability, the stability, solubility and formulation properties and the smell of a substance.

Therefore, the problem underlying the present invention has been developing new antimicrobial agents that fulfills the complex profile explained above and is particularly active at low concentrations against a variety of different micro-organisms.

DESCRIPTION OF THE INVENTION

Object of the present invention is an antimicrobial composition comprising
(a) at least one acetophenone derivative of formula (I)

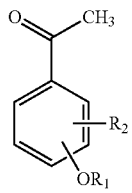

in which $R_1$ stands for hydrogen or methyl, and $R_2$ stands for hydrogen, hydroxyl or a —$OCH_3$ group, or a cosmetically or pharmaceutically acceptable salt thereof, and
(b1) at least one second antimicrobial agent selected from the group consisting of preservatives selected from the group consisting of benzoic acid and para-hydroxybenzoic acid, their esters and salts, benzyl benzoate, propionic acid and its salts, salicylic acid and its salts, 2,4-hexadienoic acid (sorbic acid) and its salts, levulinic acid and its salts, anisic acid and its salts, perillic acid and its salts, cinnamic acid and its salts, formaldehyde and paraformaldehyde, 4-hydroxy benzaldehyde, ortho-, meta-, and para-anisic aldehyde, cinnamic aldehyde, cinnamic alcohol, 2-hydroxybiphenyl ether and its salts, 2-zinc-sulfidopyridine N-oxide, inorganic sulfites and bisulfites, sodium iodate, chlorobutanolum, 4-ethylmercury-(II)5-amino-1,3-bis(2-hydroxybenzoic acid), its salts and esters, dehydracetic acid, formic acid, 1,6-bis(4-amidino-2-bromophenoxy)-n-hexane and its salts, the sodium salt of ethylmercury-(II)-thiosalicylic acid, phenylmercury and its salts, 10-undecylenic acid and its salts, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly(hexamethylenediguanide)hydrochloride, (Benzyloxymethoxy)-methanol hexamethylenetetramine, 1-(3-chloroallyl)-3,5,7-triaza-1-azonia-adamantane chloride, 1-(4-chlorophenoxy)-1-(1H-imidazol-1-yl)-3,3-dimethyl-2-butanone, 1,3-bis(hydroxymethyl)-5,5-dimethyl-2,4-imidazolidinedione, 1,2-dibromo-2,4-dicyanobutane, 2,2'-methylene-bis(6-bromo-4-chlorophenol), bromochlorophene, mixture of 5-chloro-2-methyl-3(2H)-isothiazolinone, 2-methyl-3(2H)-isothiazolinone and with magnesium chloride and magnesium nitrate, 2-Octyl-2H-isothiazol-3-one, 1,2-benzisothiazol-3(2H)-one, 2-benzyl-4-chlorophenol, 3-(4-Chlorphenoxy)-1,2-propanediol (Chlorphenesin), 2-chloroacetamide, chlorhexidine, chlorhexidine acetate, chlorhexidine gluconate, chlorhexidine hydrochloride, N-alkyl($C_{12}$-$C_{22}$)trimethylammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxy-methylurea, 1,6-bis(4-amidino-phenoxy)-n-hexane and its salts, glutaraldehyde, 5-ethyl-1-aza-3,7-dioxabicyclo(3.3.0)octane, 3-(4-chlorophenoxy)-1,2-propanediol, hyamines, alkyl-($C_8$-$C_{18}$)-dimethyl-benzyl-ammonium chloride, alkyl-($C_8$-$C_{18}$)-dimethyl-benzylammonium bromide, alkyl-($C_8$-$C_{18}$)-dimethyl-benzyl-ammonium saccharinate, benzyl hemiformal, 3-iodo-2-propynyl butylcarbamate, sodium hydroxymethyl-aminoacetate or sodium hydroxymethyl-aminoacetate, imidazolidinylurea, diazolidinylurea, sodium hydroxymethylglycinate, DMDM hydantoin, Tropolone, (Ethylendioxy)dimethanol, 2-Brom-2-(brommethyl)pentandinitril, N-(3-Aminopropyl)-N-dodecylpropan-1,3-diamin, α,α',α"-trimethyl-1,3,5-triazine-1,3,5(2H,4H,6H)-triethanol, pyridine-2-thiol-1-oxide, sodium salt, Tetrahydro-1,3,4,6-tetrakis(hydroxymethyl)imidazo[4,5-d]imidazol-2,5(1H,3H)-dion, 1,3-bis(hydroxymethyl)-1-(1,3,4-tris(hydroxy-methyl)-2,5-dioxoimidazolidin-4-yl) urea (Diazolidinyl Urea), 1,3-Bis(hydroxy-methyl)-5,5-dimethylimidazolidine-2,4-dione, 3-Acetyl-2-hydroxy-6-methyl-4H-pyran-4-one, cetyl pyridium chloride, caprylhydroxamic acid, sorbohydroxamic acid and their mixtures; and/or
(b2) at least one a second antimicrobial agent selected from the group consisting of 1,3-propanediol, methyl propanediol, 1,2-pentanediol, 1,2-hexanediol, 1,2-octanediol, 1,2-decanediol, 1,5-pentanediol, 1,6-hexanediol, 1,8-octanediol, 1,2-decanediol, ethylhexylglycerin, hexoxy-propan-1,2-diol, heptoxy-propan-1,2-diol, octoxy-propan-1,2-diol, 3-phenoxy-propan-1,2-diol, 3-benzyloxy-propan-1,2-diol, 3-phenylethyloxy-propan-1,2-diol, 3-phenylpropyloxy-propan-1,2-diol, 3-methylbenzyloxy-propan-1,2-diol, sorbitan caprylate, triclosan, climbazole, Octopirox (1-hydroxy-4-methyl-6-(2,4,4-trimethylpentyl)-2(1H)-pyridone, 2-aminoethanol), chitosan, farnesol, 2-butyloctanoic acid, 2-Benzylheptan-1-ol, glycerol monolaurate, bis(2-pyridylthio)zinc 1,1'-dioxide, N,N'-(decane-1,10-diyldipyridin-1-yl-4-ylidene)-dioctan-1-amine dihydrochloride (octenidine dihydrochloride), thymol, eugenol, benzyl alcohol, 2-phenyethyl alcohol, 3-phenyl propanol, 2-phenoxyethanol, 1-phenoxy-propan-2-ol, 3-phenoxypropanol, benzyloxymethanol.

The invention is based on the surprising finding that compounds of formula (I) according to the invention show a very good broad spectrum activity as agent to preserve various formulations against microbial spoilage. Furthermore, compounds of formula (I) synergistically intensified antimicrobial effects at least against selected microorganisms, in particular against mould species of the genus *Aspergillus*, such as *Aspergillus brasiliensis, niger, flavus, fumigatus* and also other microorganisms. Moulds are known to be combated only with great difficulty, due to their high tolerance for different pH, temperature, osmotic pressure and nutrient conditions as well as their ability to resist to and degrade different chemicals.

In particular, it has been found that the mixtures according to the invention can be used outstandingly as an antimicrobial active compound mixture, in particular for preserving otherwise perishable articles.

More particularly it was found that the synergistically active mixtures according to the invention have a good action against *Staphylococcus epidermidis, Corynebacterium xerosis, Brevibacterium epidermidis, Propionibacte-*

*rium acnes* and against *Trichophyton* and *Epidermophyton* species, so that they can be employed as agents for the treatment or the combating of underarm and foot odour or body odour generally, as agents for combating acne, as antidandruff agents and for the treatment of mycoses, in particular dermatomycoses.

Acetophenone Derivatives

Acetophenone derivatives according to the present invention represent known compounds that can be obtained by ordinary methods of organic chemistry. It is understood that both substituents $OR_1$ and $R_2$ can be located in ortho, meta or para position towards the methylketo group.

Preferably, the species are selected from the group consisting of

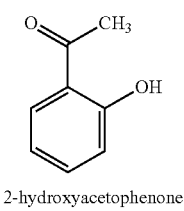

2-hydroxyacetophenone (Ia)

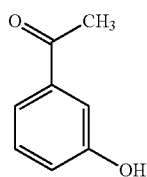

3-hydroxyacetophenone (Ib)

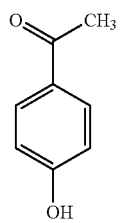

4-hydroxyacetophenone (Ic)

or their mixtures. In as far the definition refers to cosmetically or pharmaceutically acceptable salts of said derivatives, this means that these salts can be safely used for pharmaceutical purposes. This does not mean that the present invention or any aspect thereof is restricted to the use of a compound of formula (I) or a corresponding mixture for pharmaceutical purposes. Generally, if a salt can be used for pharmaceutical purposes it can likewise be used for cosmetic purposes, or in food or beverage formulations. In particular, the sodium and potassium and ammonium salts of compounds of formula (I) are considered as (pharmaceutically) acceptable salts. In some cases the utilization of the respective ionic compound or solvate carrier proves to be superior to the unmodified derivative. The (pharmaceutically) acceptable salts (and the corresponding solvates) of compounds of formula (I) can be prepared by standard procedures. Hereinafter, any reference to a compound of formula (I) or a corresponding mixture as defined above is to be understood as comprising an additional reference to corresponding (pharmaceutically) acceptable salts thereof.

It is also worth to be mentioned that although persons skilled in the art have already addressed the antimicrobial properties of aromatic alcohols, such as e.g. benzyl alcohol, 2-phenylethyl alcohol, 3-Phenylpropanol, 2-phenoxyethanol, 3-phenoxypropanol, 1-phenoxy-propan-2-ol, 3-phenoxy-propane-1,2-diol, benzyloxymethanol and (benzyloxymethoxy)-methanol extensively, there has hitherto been no indication that mixtures of the acetophenone derivatives have a significantly improved antimicrobial action (at least against selected microorganisms) in the individual case. It was therefore particularly surprising that the mixtures according to the invention show a highly synergistic activity, and in the treatment moulds of the genus *Aspergillus* are significantly superior to individually dosed compounds of the formula (I) or
individually dosed further antimicrobially active compounds not being compounds of formula (I), in particular individually dosed diols and aromatic alcohols, such as e.g. 1,3-propanediol, methyl propanediol, 1,2-pentanediol, 1,2-hexanediol, 1,2-octanediol, ethylhexylglycerin, hexoxy-propan-1,2-diol, heptoxy-propan-1,2-diol, octoxy-propan-1,2-diol, 3-benzyloxy-propan-1,2-diol, 3-phenylethyloxy-propan-1,2-diol, 3-phenylpropyloxy-propan-1,2-diol, 3-methylbenzyloxy-propan-1,2-diol, 3-phenyl propanol, 2-phenoxyethanol and mixtures of these compounds at the same concentration, in particular in respect of the reduction in microbial counts and the speed of the reduction in microbial count.

In a preferred embodiment the antimicrobial agent comprises or contains two or three of the compounds (Ia), (Ib) and (Ic), as for example 2-hydroxyacetophenone and 3-hydroxyacetophenone, or 2-hydroxyacetophenone and 4-hydroxyacetophenone, or 3-hydroxyacetophenone and 4-hydroxyacetophenone.

Preservation Mixtures

Present invention is directed to mixtures of antimicrobial agents. The mixtures may contain components (a) and (b) in a weight ratio of about 1:99 to about 99:1, preferably about 20:80 to about 80:20 and more preferably about 40:60 to about 60:40.

Additives to Preservation Mixtures

In a preferred embodiment the performance of the acetophenone derivatives or the mixtures are improved by adding certain hydroxy compounds, selected from the group consisting of 1,3-propanediol, methyl propanediol, 1,2-pentanediol, 1,2-hexanediol, 1,2-octanediol, ethylhexylglycerin, hexoxy-propan-1,2-diol, heptoxy-propan-1,2-diol, octoxy-propan-1,2-diol, 3-benzyloxy-propan-1,2-diol, 3-phenylethyloxy-propan-1,2-diol, 3-phenylpropyloxy-propan-1,2-diol, 3-methylbenzyloxy-propan-1,2-diol, 3-phenyl propanol, 2-phenoxyethanol and their mixtures. Adding 2-phenoxyethanol is particularly preferred. The additives can be present in an amount of about 1 to 25, preferably 2 to 20 and more preferably about 5 to 10% b.w.—calculated on the total mixtures.

INDUSTRIAL APPLICATION

Personal Care Compositions

Another embodiment of the present invention covers a personal care or cosmetic composition comprising a working amount of at least one acetophenone derivative or its mixtures with additional preservatives and/or antimicrobial agents, which might be present in amounts of from about 0.01 to about 10, preferably about 0.05 to about 5 and more preferably about 0.1 to about 1% b.w.—calculated on the total composition.

The personal care or cosmetic compositions may contain abrasives, antiacne agents, agents against ageing of the skin, anticellulitis agents, antidandruff agents, antiinflammatory agents, irritation-preventing agents, irritation-inhibiting agents, antioxidants, astringents, perspiration-inhibiting agents, antiseptic agents, antistatics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxy-fatty acids, liquefiers, dyestuffs, colour-protecting agents, pigments, anticorrosives, aromas, flavouring substances, odoriferous substances, polyols, surfactants, electrolytes, organic solvents or silicone derivatives and the like as additional auxiliaries and additives.

Surfactants

Other preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:
   products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
   $C_{12/18}$ fatty acid monoesters and diesters of addition products of 1 to 30 mol ethylene oxide onto glycerol;
   glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric emulsifiers. Other suitable emulsifiers are amphboteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminum and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
- p-aminobenzoic acid
- p-aminobenzoic acid ethyl ester (25 mol) ethoxylated (INCI name: PEG-25 PABA)
- p-dimethylaminobenzoic acid-2-ethylhexyl ester
- p-aminobenzoic acid ethyl ester (2 mol) N-propoxylated
- p-aminobenzoic acid glycerol ester
- salicylic acid homomenthyl ester (homosalates) (Neo Heliopan® HMS)
- salicylic acid-2-ethylhexyl ester (Neo Heliopan® OS)
- triethanolamine salicylate
- 4-isopropyl benzyl salicylate
- anthranilic acid menthyl ester (Neo Heliopan® MA)
- diisopropyl cinnamic acid ethyl ester
- p-methoxycinnamic acid-2-ethylhexyl ester (Neo Heliopan® AV)
- diisopropyl cinnamic acid methyl ester
- p-methoxycinnamic acid isoamyl ester (Neo Heliopan® E 1000)
- p-methoxycinnamic acid diethanolamine salt
- p-methoxycinnamic acid isopropyl ester
- 2-phenylbenzimidazole sulfonic acid and salts (Neo Heliopan® Hydro)
- 3-(4'-trimethylammonium)benzylidene bornan-2-one methyl sulfate
- beta-imidazole-4(5)-acrylic acid (urocanic acid)
- 3-(4'-sulfo)benzylidene bornan-2-one and salts
- 3-(4'-methyl benzylidene)-D,L-camphor (Neo Heliopan® MBC)
- 3-benzylidene-D,L-camphor
- N-[(2 and 4)-[2-(oxoborn-3-ylidene)methyl]benzyl]acrylamide polymer
- 4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb® HEB)
- benzylidene malonate polysiloxane (Parsol® SLX)
- glyceryl ethylhexanoate dimethoxycinnamate
- dipropylene glycol salicylate
- tris(2-ethylhexyl)-4,4',4''-(1,3,5-triazine-2,4,6-triyltriimino)tribenzoate (=2,4,6-trianilino-(p-carbo-2'-ethylhexyl-1'-oxy)-1,3,5-triazine) (Uvinul® T150)

Broadband filters which are preferably combined with one or more compounds of formula (I) in a preparation according to the present invention are selected from the group consisting of
- 2-ethylhexyl-2-cyano-3,3-diphenyl acrylate (Neo Heliopan® 303)
- ethyl-2-cyano-3,3'-diphenyl acrylate
- 2-hydroxy-4-methoxybenzophenone (Neo Heliopan® BB)
- 2-hydroxy-4-methoxybenzophenone-5-sulfonic acid
- dihydroxy-4-methoxybenzophenone
- 2,4-dihydroxybenzophenone
- tetrahydroxybenzophenone
- 2,2'-dihydroxy-4,4'-dimethoxybenzophenone
- 2-hydroxy-4-n-octoxybenzophenone
- 2-hydroxy-4-methoxy-4'-methyl benzophenone
- sodium hydroxymethoxybenzophenone sulfonate
- disodium-2,2'-dihydroxy-4,4'-dimethoxy-5,5'-disulfobenzophenone
- phenol, 2-(2H-benzotriazol-2-yl)-4-methyl-6-(2-methyl-3 (1,3,3,3-tetramethyl-1-(trimethylsilyl)oxy)disiloxanyl)propyl) (Mexoryl® XL)
- 2,2'-methylene bis-(6-(2H-benzotriazol-2-yl)-4-1,1,3,3-tetramethylbutyl)phenol) (Tinosorb® M)
- 2,4-bis-[4-(2-ethylhexyloxy)-2-hydroxyphenyl]-1,3,5-triazine
- 2,4-bis-[{(4-(2-ethylhexyloxy)-2-hydroxy}phenyl]-6-(4-methoxyphenyl)-1,3,5-triazine (Tinosorb® S)
- 2,4-bis-[{(4-(3-sulfonato)-2-hydroxypropyloxy)-2-hydroxy}phenyl]-6-(4-methoxyphenyl)-1,3,5-triazine sodium salt
- 2,4-bis-[{(3-(2-propyloxy)-2-hydroxypropyloxy)-2-hydroxy}phenyl]-6-(4-methoxyphenyl)-1,3,5-triazine
- 2,4-bis-[{4-(2-ethylhexyloxy)-2-hydroxy}phenyl]-6-[4-(2-methoxyethyl carbonyl)phenylamino]-1,3,5-triazine
- 2,4-bis-[{4-(3-(2-propyloxy)-2-hydroxypropyloxy)-2-hydroxy}phenyl]-6-[4-(2-ethylcarboxyl)phenylamino]-1,3,5-triazine
- 2,4-bis-[{4-(2-ethylhexyloxy)-2-hydroxy}phenyl]-6-(1-methylpyrrol-2-yl)-1,3,5-triazine
- 2,4-bis-[{4-tris-(trimethylsiloxysilylpropyloxy)-2-hydroxy}phenyl]-6-(4-methoxyphenyl)-1,3,5-triazine
- 2,4-bis-[{4-(2''-methylpropenyloxy)-2-hydroxy}phenyl]-6-(4-methoxyphenyl)-1,3,5-triazine
- 2,4-bis-[{4-(1',1',1',3',5',5',5'-heptamethylsiloxy-2''-methylpropyloxy)-2-hydroxy}phenyl]-6-(4-methoxyphenyl)-1,3,5-triazine UV-A filters filters which are preferably combined with one or more compounds of formula (I) in a preparation according to the present invention are selected from the group consisting of
- 4-isopropyl dibenzoyl methane
- terephthalylidene dibornane sulfonic acid and salts (Mexoryl® SX)
- 4-t-butyl-4'-methoxydibenzoyl methane (avobenzone)/(Neo Heliopan® 357)
- phenylene bis-benzimidazyl tetrasulfonic acid disodium salt (Neo Heliopan® AP)
- 2,2'-(1,4-phenylene)-bis-(1H-benzimidazole-4,6-disulfonic acid), monosodium salt
- 2-(4-diethylamino-2-hydroxybenzoyl)benzoic acid hexyl ester (Uvinul® A Plus)
- indanylidene compounds in accordance with DE 100 55 940 A1 (=WO 2002 038537 A1)

UV filters which are more preferably combined with one or more compounds of formula (I) in a preparation according to the present invention are selected from the group consisting of
- p-aminobenzoic acid
- 3-(4'-trimethylammonium)benzylidene bornan-2-one methyl sulfate
- salicylic acid homomenthyl ester (Neo Heliopan® HMS)
- 2-hydroxy-4-methoxybenzophenone (Neo Heliopan® BB)
- 2-phenylbenzimidazole sulfonic acid (Neo Heliopan® Hydro)
- terephthalylidene dibornane sulfonic acid and salts (Mexoryl® SX)
- 4-tert-butyl-4'-methoxydibenzoyl methane (Neo Heliopan® 357)
- 3-(4'-sulfo)benzylidene bornan-2-one and salts
- 2-ethylhexyl-2-cyano-3,3-diphenyl acrylate (Neo Heliopan® 303)

N-[(2 and 4)-[2-(oxoborn-3-ylidene)methyl]benzyl]acrylamide polymer p-methoxycinnamic acid-2-ethylhexyl ester (Neo Heliopan® AV)

p-aminobenzoic acid ethyl ester (25 mol) ethoxylated (INCI name: PEG-25 PABA)

p-methoxycinnamic acid isoamyl ester (Neo Heliopan® E1000)

2,4,6-trianilino-(p-carbo-2'-ethylhexyl-1'-oxy)-1,3,5-triazine (Uvinul® T150)

phenol, 2-(2H-benzotriazol-2-yl)-4-methyl-6-(2-methyl-3 (1,3,3,3-tetramethyl-1-(trimethylsilyl)oxy)disiloxanyl)propyl) (Mexoryl® XL)

4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)

3-(4'-methyl benzylidene)-D,L-camphor (Neo Heliopan® MBC)

3-benzylidene camphor salicylic acid-2-ethylhexyl ester (Neo Heliopan® OS)

4-dimethylaminobenzoic acid-2-ethylhexyl ester (Padimate O)

hydroxy-4-methoxybenzophenone-5-sulfonic acid and Na salt 2,2'-methylene bis-(6-(2H-benzotriazol-2-yl)-4-1,1,3,3-tetramethylbutyl)phenol) (Tinosorb® M)

phenylene bis-benzimidazyl tetrasulfonic acid disodium salt (Neo Heliopan® AP)

2,4-bis-[{(4-(2-ethylhexyloxy)-2-hydroxy}phenyl]-6-(4-methoxyphenyl)-1,3,5-triazine (Tinosorb® S)

benzylidene malonate polysiloxane (Parsol® SLX)

menthyl anthranilate (Neo Heliopan® MA)

2-(4-diethylamino-2-hydroxybenzoyl)benzoic acid hexyl ester (Uvinul® A Plus)

indanylidene compounds in accordance with DE 100 55 940 (=WO 02/38537).

Secondary Sun Protection Factors

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminum ($Al_2O_3$), cerium (e.g. $Ce_2O_3$) and/or mixtures thereof.

Anti-Ageing Actives

In the context of the invention, anti-ageing or biogenic agents are, for example antioxidants, matrix-metalloproteinase inhibitors (MMPI), skin moisturizing agents, glycosaminglycan stimulators, anti-inflammatory agents, TRPV1 antagonists and plant extracts.

Antioxidants. Amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, *melissa*, thyme, lavender, olive, oats, cocoa, *ginkgo*, ginseng, liquorice, honeysuckle, *sophora, pueraria, pinus, citrus, Phyllanthus emblica* or St. John's wort, grape seeds, wheat germ, *Phyllanthus emblica*, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-moisturizing agents. Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan stimulators. Preferred compositions comprise substances stimulating the synthesis of glycosaminoglycans selected from the group consisting of hyaluronic acid and derivatives or salts, Subliskin (Sederma, INCI: *Sinorhizobium Meliloti* Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, *Sinorhizobium Meliloti* Ferment Filtrate, Calcium ketogluconate, *Alpinia galanga* leaf extract and tetradecyl aminobutyroylvalylaminobutyric urea trifluoroacetate.

Anti-inflammatory agents. The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, *Aloe vera, Commiphora* species, *Rubia* species, willow, willow-herb, oats, calendula, arnica, St John's wort, honeysuckle, rosemary, *Passiflora incarnata*, witch hazel, ginger or *Echinacea*; preferably selected from the group consisting of extracts or fractions from camomile, *Aloe vera*, oats, calendula, arnica, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occurring avenanthramides, preferably tranilast, avenanthramide A, avenanthramide B, avenanthramide C, non-natural or non-naturally occurring avenanthramides, preferably dihydroavenanthramide D, dihydroavenanthramide E, avenanthramide D, avenanthramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

Botanical extracts. The compositions may also contain various extracts of plants, such as for example extracts of *Ginkgo biloba, Oleacea europensis, Glyzyrrhiza glabra, Vaccinium myrtillus, Trifolium pratense, Litchi sinensis, Vitis, vinifera, Brassica oleracea, Punica granatum, Petroselinium crispum, Centella asiatica, Passiflora incarnata, Medicago sativa, Melissa officinalis, Valeriana officinalis, Castanea sativa, Salix alba* and *Hapagophytum procumbens*.

Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (l-menthoxy)-1,2-propandiol, (l-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^{\alpha}$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (l-(−)-isopulegol, l-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminum, zirconium or of zinc. Such suitable antihydrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminum pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;
amino sugars, for example glucamine;
dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, ·-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, *melissa* oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3, Fe_3O_4$, FeO (OH)) and/or tin oxide. Advantageous dyes are for example carmine, Berlin blue, chromium oxide green, ultramarine blue and/or manganese violet.

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

Detergent Compositions

Another embodiment of the present invention covers a detergent composition comprising a working amount of at least one acetophenone derivative or its mixtures with additional preservatives and/or antimicrobial agents, which might be present in amounts of from about 0.01 to about 10, preferably about 0.05 to about 5 and more preferably about 0.1 to about 1% b.w.—calculated on the total composition.

The detergent compositions according to the present invention may comprise any of the ingredients customarily found in such compositions, such as, for example, anionic, nonionic, cationic, amphoteric or zwitterionic (co-)surfactants, organic solvents, builders, enzymes and additional auxiliaries such as soil repellents, thickeners, colorants and fragrances or the like.

Anionic (Co-)Surfactants

Preferably, surfactants of the sulfonate type, alk(en)yl sulfonates, alkoxylated alk(en)yl sulfates, ester sulfonates and/or soaps are used as the anionic surfactants. Suitable surfactants of the sulfonate type are advantageously $C_{9-13}$ alkylbenzene sulfonates, olefin sulfonates, i.e. mixtures of alkene- and hydroxyalkane sulfonates, and disulfonates, as are obtained, for example, by the sulfonation with gaseous sulfur trioxide of $C_{12-18}$ monoolefins having a terminal or internal double bond and subsequent alkaline or acidic hydrolysis of the sulfonation products.

Alk(en)yl sulfates. Preferred alk(en)yl sulfates are the alkali and especially the sodium salts of the sulfuric acid half-esters of the $C_{12}$-$C_{18}$ fatty alcohols, for example, from coconut butter alcohol, tallow alcohol, lauryl, myristyl, cetyl or stearyl alcohol or from $C_8$-$C_{20}$ oxo alcohols and those half-esters of secondary alcohols of these chain lengths. Alk(en)yl sulfates of the cited chain lengths that comprise a synthetic straight chain alkyl group manufactured petrochemically are also preferred. The $C_{12}$-$C_{16}$ alkyl sulfates and $C_{12}$-$C_{15}$ alkyl sulfates as well as $C_{14}$-$C_{15}$ alkyl sulfates and $C_{14}$-$C_{16}$ alkyl sulfates are particularly preferred on the grounds of laundry performance. The 2,3-alkyl sulfates, which can be obtained from Shell Oil Company under the trade name DAN™, are also suitable anionic surfactants.

Alk(en)yl ether sulfates. Sulfuric acid mono-esters derived from straight-chained or branched $C_7$-$C_{21}$ alcohols ethoxylated with 1 to 6 moles ethylene oxide are also suitable, such as 2-methyl-branched $C_9$-$C_{11}$ alcohols with an average of 3.5 mol ethylene oxide (EO) or $C_{12}$-$C_{18}$ fatty alcohols with 1 to 4 EO.

Ester sulfonates. The esters of alpha-sulfo fatty acids (ester sulfonates), e.g., the alpha-sulfonated methyl esters of hydrogenated coco-, palm nut- or tallow acids are likewise suitable.

Soaps. Soaps, in particular, can be considered as further anionic surfactants. Saturated fatty acid soaps are particularly suitable, such as the salts of lauric acid, myristic acid, palmitic acid, stearic acid, hydrogenated erucic acid and behenic acid, and especially soap mixtures derived from natural fatty acids such as coconut oil fatty acid, palm kernel oil fatty acid or tallow fatty acid. Those soap mixtures are particularly preferred that are composed of 50 to 100 wt. % of saturated $C_{12}$-$C_{24}$ fatty acid soaps and 0 to 50 wt. % of oleic acid soap.

Ether carboxylic acids. A further class of anionic surfactants is that of the ether carboxylic acids, obtainable by treating fatty alcohol ethoxylates with sodium chloroacetate in the presence of basic catalysts. They have the general formula: $RO(CH_2CH_2O)_pCH_2COOH$ with R=$C_1$-$C_{18}$ and p=0.1 to 20. Ether carboxylic acids are insensitive to water hardness and possess excellent surfactant properties.

Nonionic (Co-)Surfactants

Alkohol alkoxylates. The added nonionic surfactants are preferably alkoxylated and/or propoxylated, particularly primary alcohols having preferably 8 to 18 carbon atoms and an average of 1 to 12 mol ethylene oxide (EO) and/or 1 to 10 mol propylene oxide (PO) per mol alcohol. $C_8$-$C_{16}$-Alcohol alkoxylates, advantageously ethoxylated and/or propoxylated $C_{10}$-$C_{15}$-alcohol alkoxylates, particularly $C_{12}$-$C_{14}$ alcohol alkoxylates, with an ethoxylation degree between 2 and 10, preferably between 3 and 8, and/or a propoxylation degree between 1 and 6, preferably between 1.5 and 5, are particularly preferred. The cited degrees of ethoxylation and propoxylation constitute statistical average values that can be a whole or a fractional number for a specific product. Preferred alcohol ethoxylates and propoxylates have a narrowed homolog distribution (narrow range ethoxylates/propoxylates, NRE/NRP). In addition to these nonionic surfactants, fatty alcohols with more than 12 EO can also be used. Examples of these are (tallow) fatty alcohols with 14 EO, 16 EO, 20 EO, 25 EO, 30 EO or 40 EO.

Alkylglycosides (APG®). Furthermore, as additional nonionic surfactants, alkyl glycosides that satisfy the general Formula $RO(G)_x$, can be added, e.g., as compounds, particularly with anionic surfactants, in which R means a primary linear or methyl-branched, particularly 2-methyl-branched, aliphatic group containing 8 to 22, preferably 12 to 18 carbon atoms and G stands for a glycose unit containing 5 or 6 carbon atoms, preferably for glucose. The degree of oligomerization x, which defines the distribution of monoglycosides and oligoglycosides, is any number between 1 and 10, preferably between 1.1 and 1.4.

Fatty acid ester alkoxylates. Another class of preferred nonionic surfactants, which are used either as the sole nonionic surfactant or in combination with other nonionic surfactants, in particular, together with alkoxylated fatty alcohols and/or alkyl glycosides, are alkoxylated, preferably ethoxylated or ethoxylated and propoxylated fatty acid alkyl esters preferably containing 1 to 4 carbon atoms in the alkyl chain, more particularly the fatty acid methyl esters which are described, for example, in Japanese Patent Application JP-A-58/217598 or which are preferably produced by the process described in International Patent Application WO-A-90/13533. Methyl esters of $C_{12}$-$C_{18}$ fatty acids containing an average of 3 to 15 EO, particularly containing an average of 5 to 12 EO, are particularly preferred.

Amine oxides. Nonionic surfactants of the amine oxide type, for example, N-coco alkyl-N,N-dimethylamine oxide and N-tallow alkyl-N,N-dihydroxyethylamine oxide, and the fatty acid alkanolamides may also be suitable. The quantity in which these nonionic surfactants are used is preferably no more than the quantity in which the ethoxylated fatty alcohols are used and, particularly no more than half that quantity.

Gemini surfactants. The so-called gemini surfactants can be considered as further surfactants. Generally speaking, such compounds are understood to mean compounds that have two hydrophilic groups and two hydrophobic groups per molecule. As a rule, these groups are separated from one another by a "spacer". The spacer is usually a hydrocarbon chain that is intended to be long enough such that the hydrophilic groups are a sufficient distance apart to be able to act independently of one another. These types of surfactants are generally characterized by an unusually low critical micelle concentration and the ability to strongly reduce the surface tension of water. In exceptional cases, however, not only dimeric but also trimeric surfactants are meant by the term gemini surfactants. Suitable gemini surfactants are, for example, sulfated hydroxy mixed ethers according to German Patent Application DE 4321022 A1 or dimer alcohol bis- and trimer alcohol tris sulfates and ether sulfates according to International Patent Application WO 96/23768 A1. Blocked end group dimeric and trimeric mixed ethers according to German Patent Application DE 19513391 A1 are especially characterized by their bifunctionality and multifunctionality. Gemini polyhydroxyfatty acid amides or polyhydroxyfatty acid amides, such as those described in International Patent Applications WO 95/19953 A1, WO 95/19954 A1 and WO 95/19955 A1 can also be used.

Cationic Co-Surfactants

Tetraalkyl ammonium salts. Cationically active surfactants comprise the hydrophobic high molecular group required for the surface activity in the cation by dissociation in aqueous solution. A group of important representatives of the cationic surfactants are the tetraalkyl ammonium salts of the general formula: $(R^1R^2R^3R^4N^+)X^-$. Here R1 stands for $C_1$-$C_8$ alk(en)yl, $R^2$, $R^3$ and $R^4$, independently of each other, for alk(en)yl radicals having 1 to 22 carbon atoms. X is a counter ion, preferably selected from the group of the halides, alkyl sulfates and alkyl carbonates. Cationic surfactants, in which the nitrogen group is substituted with two long acyl groups and two short alk(en)yl groups, are particularly preferred.

Esterquats. A further class of cationic surfactants particularly useful as co-surfactants for the present invention is represented by the so-called esterquats. Esterquats are generally understood to be quaternised fatty acid triethanolamine ester salts. These are known compounds which can be obtained by the relevant methods of preparative organic chemistry. Reference is made in this connection to International patent application WO 91/01295 A1, according to which triethanolamine is partly esterified with fatty acids in the presence of hypophosphorous acid, air is passed through the reaction mixture and the whole is then quaternised with dimethyl sulphate or ethylene oxide. In addition, German patent DE 4308794 C1 describes a process for the production of solid esterquats in which the quaternisation of triethanolamine esters is carried out in the presence of suitable dispersants, preferably fatty alcohols.

Typical examples of esterquats suitable for use in accordance with the invention are products of which the acyl component derives from monocarboxylic acids corresponding to formula RCOOH in which RCO is an acyl group containing 6 to 10 carbon atoms, and the amine component is triethanolamine (TEA). Examples of such monocarboxylic acids are caproic acid, caprylic acid, capric acid and technical mixtures thereof such as, for example, so-called head-fractionated fatty acid. Esterquats of which the acyl component derives from monocarboxylic acids containing 8 to 10 carbon atoms, are preferably used. Other esterquats are those of which the acyl component derives from dicarboxylic acids like malonic acid, succinic acid, maleic acid, fumaric acid, glutaric acid, sorbic acid, pimelic acid, azelaic acid, sebacic acid and/or dodecanedioic acid, but preferably adipic acid. Overall, esterquats of which the acyl component derives from mixtures of monocarboxylic acids containing 6 to 22 carbon atoms, and adipic acid are preferably used. The molar ratio of mono and dicarboxylic acids in the final esterquat may be in the range from 1:99 to 99:1 and is preferably in the range from 50:50 to 90:10 and more particularly in the range from 70:30 to 80:20. Besides the quaternised fatty acid triethanolamine ester salts, other suitable esterquats are quaternized ester salts of mono-/dicarboxylic acid mixtures with diethanolalkyamines or 1,2-dihydroxypropyl dialkyamines. The esterquats may be obtained both from fatty acids and from the corresponding triglycerides in admixture with the corresponding dicarboxylic acids. One such process, which is intended to be representative of the relevant prior art, is proposed in European patent EP 0750606 B1. To produce the quaternised esters, the mixtures of mono- and dicarboxylic acids and the triethanolamine—based on the available carboxyl functions—may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9.

Amphoteric or Zwitterionic Co-Surfactants

Betaines. Amphoteric or ampholytic surfactants possess a plurality of functional groups that can ionize in aqueous solution and thereby—depending on the conditions of the medium—lend anionic or cationic character to the compounds (see DIN 53900, July 1972). Close to the isoelectric point (around pH 4), the amphoteric surfactants form inner salts, thus becoming poorly soluble or insoluble in water. Amphoteric surfactants are subdivided into ampholytes and betaines, the latter existing as zwitterions in solution. Ampholytes are amphoteric electrolytes, i.e. compounds that possess both acidic as well as basic hydrophilic groups and therefore behave as acids or as bases depending on the conditions. Especially betaines are known surfactants which are mainly produced by carboxyalkylation, preferably carboxymethylation, of amine compounds. The starting materials are preferably condensed with halocarboxylic acids or salts thereof, more particularly sodium chloroacetate, one mole of salt being formed per mole of betaine. The addition of unsaturated carboxylic acids, such as acrylic acid for example, is also possible. Examples of suitable betaines are the carboxy alkylation products of secondary and, in particular, tertiary amines which correspond to formula $R^1R^2R^3N$—$(CH_2)_q COOX$ where $R^1$ is a an alkyl radical having 6 to 22 carbon atoms, $R^2$ is hydrogen or an alkyl group containing 1 to 4 carbon atoms, $R^3$ is an alkyl group containing 1 to 4 carbon atoms, q is a number of 1 to 6 and X is an alkali and/or alkaline earth metal or ammonium. Typical examples are the carboxymethylation products of hexylmethylamine, hexyldimethylamine, octyldimethylamine, decyldimethylamine, $C_{12/14}$-cocoalkyldimethylamine, myristyldimethylamine, cetyldimethylamine, stearyldimethylamine, stearylethylmethylamine, oleyldimethylamine, $C_{16/18}$-tallowalkyldimethylamine and their technical mixtures, and particularly dodecyl methylamine, dodecyl dimethylamine, dodecyl ethylmethylamine and technical mixtures thereof.

Alkylamido betaines. Other suitable betaines are the carboxyalkylation products of amidoamines corresponding to formula $R^1CO(R^3)(R^4)$—$NH$—$(CH_2)_p$—$N$—$(CH_2)_q COOX$ in which $R^1CO$ is an aliphatic acyl radical having 6 to 22 carbon atoms and 0 or 1 to 3 double bonds, $R^2$ is hydrogen or an alkyl radical having 1 to 4 carbon atoms, $R^3$ is an alkyl radical having 1 to 4 carbon atoms, p is a number from 1 to 6, q is a number from 1 to 3 and X is an alkali and/or alkaline earth metal or ammonium. Typical examples are reaction products of fatty acids having 6 to 22 carbon atoms, like for example caproic acid, caprylic acid, caprinic acid, lauric acid, myristic acid, palmitic acid, palmoleic acid, stearic acid, isostearic acid, oleic acid, elaidic acid, petroselinic acid, linolic acid linoleic acid, elaeostearic acid, arachidonic acid, gadoleic acid, behenic acid, erucic acid and their technical mixtures with N,N-dimethylaminoethylamine, N,N-dimethylaminopropylamine, N,N-diethylaminoethylamine and N,N-diethylaminopropylamine, which are condensed with sodium chloroacetate. The commercially available products include Dehyton® K and Dehyton® PK (Cognis Deutschland GmbH & Co., KG) as well as Tego® Betaine (Goldschmidt).

Imidazolines. Other suitable starting materials for the betaines to be used for the purposes of the invention are imidazolines. These substances are also known and may be obtained, for example, by cyclizing condensation of 1 or 2 moles of $C_6$-$C_{22}$ fatty acids with polyfunctional amines, such as for example aminoethyl ethanolamine (AEEA) or diethylenetriamine. The corresponding carboxyalkylation products are mixtures of different open-chain betaines. Typical examples are condensation products of the above-mentioned fatty acids with AEEA, preferably imidazolines based on lauric acid, which are subsequently betainised with sodium chloroacetate. The commercially available products include Dehyton® G (Cognis Deutschland GmbH & Co., KG)

The amount of (co-)surfactant comprised in the inventive compositions is advantageously 0.1 wt. % to 90 wt. %, particularly 10 wt. % to 80 wt. % and particularly preferably 20 wt. % to 70 wt.-%.

Organic Solvents

Liquid light or heavy duty detergents may comprise organic solvents, preferably those miscible with water. Polydiols, ethers, alcohols, ketones, amides and/or esters are preferably used as the organic solvent for this in amounts of 0 to 90 wt. %, preferably 0.1 to 70 wt. %, particularly 0.1 to 60 wt. %. Low molecular weight polar substances, such as for example, methanol, ethanol, propylene carbonate, acetone, acetonylacetone, diacetone alcohol, ethyl acetate, 2-propanol, ethylene glycol, propylene glycol, glycerin, diethylene glycol, dipropylene glycol monomethyl ether and dimethylformamide or their mixtures are preferred.

Enzymes

Suitable enzymes include, in particular, those from the classes of hydrolases, such as proteases, esterases, lipases or lipolytic enzymes, amylases, cellulases or other glycosyl hydrolases and mixtures thereof. In the wash, all these hydrolases contribute to removing stains such as protein, fat or starchy stains and against graying. Moreover, cellulases and other glycosyl hydrolases can contribute to increased softness of the textile and to color retention by removing pilling and micro fibrils. Oxidoreductases can also be added to the bleaches or to inhibit the color transfer. Enzymatic active materials obtained from bacterial sources or fungi such as *Bacillus subtilis, Bacillus licheniformis, Streptomyceus griseus* and *Humicola insolens* are particularly well suited. Proteases of the subtilisin type and particularly proteases that are obtained from *bacillus lentus* are preferably used. Here, mixtures of enzymes are of particular interest, for example, proteases and amylases or proteases and lipases or lipolytic enzymes or proteases and cellulases or cellulases and lipase or lipolytic enzymes or proteases, amylases and lipases or lipolytic enzymes or proteases, lipases or lipolytic enzymes and cellulases, in particular, however proteases and/or lipase-containing mixtures or mixtures with lipolytic enzymes. Examples of such lipolytic enzymes are the known cutinases. Peroxidases or oxidases have also proved to be suitable in certain cases. The suitable amylases particularly include .alpha.-amylases, iso-amylases, pullulanases and pectinases. Cellobiohydrolases, endoglucanases and .beta.-glucosidases or mixtures thereof, which are also known as cellobiases, are preferred cellulases. As the different cellulase types differ in their CMCase and avicelase activities, the required activities can be adjusted by controlled mixtures of the cellulases. The content of the enzymes or enzyme mixtures may be, for example, about 0.1 to 5% by weight and is preferably 0.1 to about 3% by weight.

Builders

Zeolites. Fine crystalline, synthetic zeolites containing bound water can be used as builders, for example, preferably zeolite A and/or P. Zeolite MAP® (commercial product of the Crosfield company), is particularly preferred as the zeolite P. However, zeolite X and mixtures of A, X, Y and/or P are also suitable. A co-crystallized sodium/potassium aluminum silicate from Zeolite A and Zeolite X, which is available as Vegobond® RX. (commercial product from Condea Augusta S.p.A.), is also of particular interest. Preferably, the zeolite can be used as a spray-dried powder. For the case where the zeolite is added as a suspension, this can comprise small amounts of nonionic surfactants as stabilizers, for example, 1 to 3 wt. %, based on the zeolite, of ethoxylated $C_{12}$-$C_{18}$ fatty alcohols with 2 to 5 ethylene oxide groups, $C_{12}$-$C_{14}$ fatty alcohols with 4 to 5 ethylene oxide groups or ethoxylated isotridecanols. Suitable zeolites have an average particle size of less than 10 µm (test method: volumetric distribution Coulter counter) and preferably comprise 18 to 22 wt. %, particularly 20 to 22 wt. % of bound water. Apart from this, phosphates can also be used as builders.

Layered silicates. Suitable substitutes or partial substitutes for phosphates and zeolites are crystalline, layered sodium silicates. These types of crystalline layered silicates are described, for example, in European Patent Application EP 0164514 A1. Preferred crystalline layered silicates are those obtained for example, from the process described in International Patent Application WO 91/08171 A1.

Amorphous silicates. Preferred builders also include amorphous sodium silicates with a modulus ($Na_2O$:$SiO_2$ ratio) of 1:2 to 1:3.3, preferably 1:2 to 1:2.8 and more preferably 1:2 to 1:2.6, which dissolve with a delay and exhibit multiple wash cycle properties. The delay in dissolution compared with conventional amorphous sodium silicates can have been obtained in various ways, for example, by surface treatment, compounding, compressing/compacting or by over-drying. In the context of this invention, the term "amorphous" also means "X-ray amorphous". In other words, the silicates do not produce any of the sharp X-ray reflexions typical of crystalline substances in X-ray diffraction experiments, but at best one or more maxima of the scattered X-radiation, which have a width of several degrees of the diffraction angle. However, particularly good builder properties may even be achieved where the silicate particles produce indistinct or even sharp diffraction maxima in electron diffraction experiments. This is to be interpreted to mean that the products have microcrystalline regions between 10 and a few hundred nm in size, values of up to at most 50 nm and especially up to at most 20 nm being preferred. This type of X-ray amorphous silicates, which similarly possess a delayed dissolution in comparison with the customary water glasses, are described, for example, in German Patent Application DE 4400024 A1. Compacted/densified amorphous silicates, compounded amorphous silicates and over dried X-ray-amorphous silicates are particularly preferred.

Phosphates. Also the generally known phosphates can also be added as builders, in so far that their use should not be avoided on ecological grounds. The sodium salts of the orthophosphates, the pyrophosphates and especially the tripolyphosphates are particularly suitable. Their content is generally not more than 25 wt. %, preferably not more than 20 wt. %, each based on the finished composition. In some cases it has been shown that particularly tripolyphosphates, already in low amounts up to maximum 10 wt. %, based on the finished composition, in combination with other builders, lead to a synergistic improvement of the secondary washing power. Preferred amounts of phosphates are under 10 wt. %, particularly 0 wt. %.

Cobuilders

Polycarboxylic acids. Useful organic cobuilders are, for example, the polycarboxylic acids usable in the form of their sodium salts of polycarboxylic acids, wherein polycarboxylic acids are understood to be carboxylic acids that carry more than one acid function. These include, for example, citric acid, adipic acid, succinic acid, glutaric acid, malic acid, tartaric acid, maleic acid, fumaric acid, sugar acids, aminocarboxylic acids, nitrilotriacetic acid (NTA) and its derivatives and mixtures thereof. Preferred salts are the salts of polycarboxylic acids such as citric acid, adipic acid, succinic acid, glutaric acid, tartaric acid, sugar acids and mixtures thereof.

Organic acids. Acids per se can also be used. Besides their building effect, the acids also typically have the property of an acidifying component and, hence also serve to establish a relatively low and mild pH in detergents or cleansing compositions. Citric acid, succinic acid, glutaric acid, adipic acid, gluconic acid and any mixtures thereof are particularly mentioned in this regard. Further suitable acidifiers are the known pH regulators such as sodium hydrogen carbonate and sodium hydrogen sulfate.

Polymers. Particularly suitable polymeric cobuilders are polyacrylates, which preferably have a molecular weight of 2,000 to 20,000 g/mol. By virtue of their superior solubility, preferred representatives of this group are again the short-chain polyacrylates, which have molecular weights of 2,000 to 10,000 g/mol and, more particularly, 3,000 to 5,000 g/mol. Suitable polymers can also include substances that consist partially or totally of vinyl alcohol units or its derivatives.

Further suitable copolymeric polycarboxylates are particularly those of acrylic acid with methacrylic acid and of acrylic acid or methacrylic acid with maleic acid. Copolymers of acrylic acid with maleic acid, which comprise 50 to 90 wt. % acrylic acid and 50 to 10 wt. % maleic acid, have proven to be particularly suitable. Their relative molecular weight, based on free acids, generally ranges from 2,000 to 70,000 g/mol, preferably 20,000 to 50,000 g/mol and especially 30,000 to 40,000 g/mol. The (co)polymeric polycarboxylates can be added either as an aqueous solution or preferably as powder. In order to improve the water solubility, the polymers can also comprise allylsulfonic acids as monomers, such as, for example, allyloxybenzene sulfonic acid and methallyl sulfonic acid as in the EP 0727448 B1.

Biodegradable polymers comprising more than two different monomer units are particularly preferred, examples being those comprising, as monomers, salts of acrylic acid and of maleic acid, and also vinyl alcohol or vinyl alcohol derivatives, as in DE 4300772 A1, or those comprising, as monomers, salts of acrylic acid and of 2-alkylallyl sulfonic acid, and also sugar derivatives. Further preferred copolymers are those that are described in German Patent Applications DE 4303320 A1 and DE 4417734 A1 and preferably include acrolein and acrylic acid/acrylic acid salts or acrolein and vinyl acetate as monomers.

Similarly, other preferred builders are polymeric aminodicarboxylic acids, salts or precursors thereof. Those polyaspartic acids or their salts and derivatives disclosed in German Patent Application DE 19540086 A1 as having a bleach-stabilizing action in addition to cobuilder properties are particularly preferred.

Further suitable builders are polyacetals that can be obtained by treating dialdehydes with polyol carboxylic acids that possess 5 to 7 carbon atoms and at least 3 hydroxyl groups, as described in European Patent Application EP 0280223 A1. Preferred polyacetals are obtained from dialdehydes like glyoxal, glutaraldehyde, terephthalaldehyde as well as their mixtures and from polycarboxylic acids like gluconic acid and/or glucoheptonic acid.

Carbohydrates. Further suitable organic cobuilders are dextrins, for example, oligomers or polymers of carbohydrates that can be obtained by the partial hydrolysis of starches. The hydrolysis can be carried out using typical processes, for example, acidic or enzymatic catalyzed processes. The hydrolysis products preferably have average molecular weights in the range of 400 to 500,000 g/mol. A polysaccharide with a dextrose equivalent (DE) of 0.5 to 40 and, more particularly, 2 to 30 is preferred, the DE being an accepted measure of the reducing effect of a polysaccharide in comparison with dextrose, which has a DE of 100. Both maltodextrins with a DE between 3 and 20 and dry glucose syrups with a DE between 20 and 37 and also so-called yellow dextrins and white dextrins with relatively high molecular weights of 2,000 to 30,000 g/mol may be used. A preferred dextrin is described in British Patent Application 94 19 091.

The oxidized derivatives of such dextrins concern their reaction products with oxidizing compositions that are capable of oxidizing at least one alcohol function of the saccharide ring to the carboxylic acid function. Such oxidized dextrins and processes for their manufacture are known for example, from European Patent Applications EP 0232202 A1. A product oxidized at C6 of the saccharide ring can be particularly advantageous.

Oxydisuccinates and other derivatives of disuccinates, preferably ethylenediamine disuccinate are also further suitable cobuilders. Here, ethylene diamine-N,N'-disuccinate (EDDS), the synthesis of which is described for example, in U.S. Pat. No. 3,158,615, is preferably used in the form of its sodium or magnesium salts. In this context, glycerine disuccinates and glycerine trisuccinates are also particularly preferred, such as those described in U.S. Pat. No. 4,524,009. Suitable addition quantities in zeolite-containing and/or silicate-containing formulations range from 3 to 15% by weight.

Lactones. Other useful organic co-builders are, for example, acetylated hydroxycarboxylic acids and salts thereof which optionally may also be present in lactone form and which contain at least 4 carbon atoms, at least one hydroxyl group and at most two acid groups. Such cobuilders are described, for example, in International Patent Application WO 95/20029 A1.

Soil Repellents

In addition, the compositions can also comprise components that positively influence the oil and fat removal from textiles during the wash (so-called soil repellents). This effect is particularly noticeable when a textile is dirty and had been previously already washed several times with an inventive detergent that comprised this oil- or fat-removing component. The preferred oil and fat removing components include, for example, nonionic cellulose ethers such as methyl cellulose and methyl hydroxypropyl cellulose with a content of methoxy groups of 15 to 30 wt. % and hydroxypropoxy groups of 1 to 15 wt. %, each based on the nonionic cellulose ether, as well as polymers of phthalic acid and/or terephthalic acid or their derivatives known from the prior art, particularly polymers of ethylene terephthalates and/or polyethylene glycol terephthalates or anionically and/or nonionically modified derivatives thereof. From these, the sulfonated derivatives of the phthalic acid polymers and the terephthalic acid polymers are particularly preferred.

Inorganic Salts

Further suitable ingredients of the composition are water-soluble inorganic salts such as bicarbonates, carbonates, amorphous silicates or mixtures of these; alkali carbonate and amorphous silicate are particularly used, principally sodium silicate with a molar ratio $Na_2O:SiO_2$ of 1:1 to 1:4.5, preferably of 1:2 to 1:3.5. Preferred compositions comprise alkaline salts, builders and/or cobuilders, preferably sodium carbonate, zeolite, crystalline, layered sodium silicates and/or trisodium citrate, in amounts of 0.5 to 70 wt. %, preferably 0.5 to 50 wt. %, particularly 0.5 to 30 wt. % anhydrous substance.

Foam Inhibitors

Especially when used in automatic washing processes, it can be advantageous to add conventional foam inhibitors to the compositions. Suitable foam inhibitors include for example, soaps of natural or synthetic origin, which have a high content of $C_{18}$-$C_{24}$ fatty acids. Suitable non-surface-active types of foam inhibitors are, for example, organopolysiloxanes and mixtures thereof with microfine, optionally silanised silica and also paraffins, waxes, microcrystalline waxes and mixtures thereof with silanised silica or bis-stearyl ethylene-diamide. Mixtures of various foam inhibitors, for example, mixtures of silicones, paraffins or waxes, are also used with advantage. Preferably, the foam inhibitors, especially silicone-containing and/or paraffin-containing foam inhibitors, are loaded onto a granular, water-soluble or dispersible carrier material. Especially in this case, mixtures of paraffins and bis-stearylethylene diamides are preferred.

Sequestrants

The salts of polyphosphonic acid can be considered as sequestrants or as stabilizers, particularly for peroxy compounds and enzymes, which are sensitive towards heavy metal ions. Here, the sodium salts of, for example, 1-hydroxyethane-1,1-diphosphonate, diethylenetriamine pentamethylene phosphonate or ethylenediamine tetramethylene phosphonate are used in amounts of 0.1 to 5 wt. %.

Graying Inhibitors

Graying inhibitors have the function of maintaining the dirt that was removed from the fibers suspended in the washing liquor, thereby preventing the dirt from resettling. Water-soluble colloids of mostly organic nature are suitable for this, for example, the water-soluble salts of (co)polymeric carboxylic acids, glue, gelatins, salts of ether carboxylic acids or ether sulfonic acids of starches or celluloses, or salts of acidic sulfuric acid esters of celluloses or starches. Water-soluble, acid group-containing polyamides are also suitable for this purpose. Moreover, soluble starch preparations and others can be used as the above-mentioned starch products, e.g., degraded starches, aldehyde starches etc. Polyvinyl pyrrolidone can also be used. Preference, however, is given to the use of cellulose ethers such as carboxymethyl cellulose (Na salt), methyl cellulose, hydroxyalkyl celluloses and mixed ethers such as methyl hydroxyethyl cellulose, methyl hydroxypropyl cellulose, methyl carboxymethyl cellulose and mixtures thereof, as well as polyvinyl pyrrolidone, which can be added, for example, in amounts of 0.1 to 5 wt. %, based on the composition.

Optical Brighteners and UV Adsorbers

The compositions may comprise e.g., derivatives of diaminostilbene disulfonic acid or alkali metal salts thereof as the optical brighteners. Suitable optical brighteners are, for example, salts of 4,4'-bis-(2-anilino-4-morpholino-1,3, 5-triazinyl-6-amino)stilbene-2,2'-disulfonic acid or compounds of similar structure which contain a diethanolamino group, a methylamino group, an anilino group or a 2-methoxyethylamino group instead of the morpholino group. Brighteners of the substituted diphenylstyryl type may also be present, for example, the alkali metal salts of 4,4'-bis(2-sulfostyryl)diphenyl, 4,4'-bis(4-chloro-3-sulfostyryl)diphenyl or 4-(4-chlorostyryl)-4'-(2-sulfostyryl)diphenyl. Mixtures of the mentioned brighteners may also be used.

In addition, UV absorbers may also be added. These are compounds with distinct absorption abilities for ultra violet radiation, which contribute as UV stabilizers as well as to improve the light stability of colorants and pigments both for textile fibers as well as for the skin of the wearer of textile products by protecting against the UV radiation that penetrates the fabric. In general, the efficient radiationless deactivating compounds are derivatives of benzophenone, substituted with hydroxyl and/or alkoxy groups, mostly in position(s) 2 and/or 4. Also suitable are substituted benzotriazoles, additionally acrylates that are phenyl-substituted in position 3 (cinnamic acid derivatives), optionally with cyano groups in position 2, salicylates, organic Ni complexes, as well as natural substances such as umbelliferone and the endogenous urocanic acid. In a preferred embodiment, the UV absorbers absorb UV-A and UV-B radiation as well as possible UV-C radiation and re-emit light with blue wavelengths, such that they additionally have an optical brightening effect. Preferred UV absorbers encompass triazine derivatives, e.g., hydroxyaryl-1,3,5-triazine, sulfonated 1,3,5-triazine, o-hydroxyphenylbenzotriazole and 2-aryl-2H-benzotriazole as well as bis(anilinotriazinylamino)stilbene disulfonic acid and their derivatives. Ultra violet absorbing pigments like titanium dioxide can also be used as UV absorbers.

Thickeners

The compositions can also comprise common thickeners and anti-deposition compositions as well as viscosity regulators such as polyacrylates, polycarboxylic acids, polysaccharides and their derivatives, polyurethanes, polyvinyl pyrrolidones, castor oil derivatives, polyamine derivatives such as quaternized and/or ethoxylated hexamethylenediamines as well as any mixtures thereof. Preferred compositions have a viscosity below 10,000 mPa·s, measured with a Brookfield viscosimeter at a temperature of 20° C. and a shear rate of 50 $min^{-1}$.

Perfumes and Colorants

The compositions can comprise further typical detergent and cleansing composition ingredients such as perfumes and/or colorants, wherein such colorants are preferred that leave no or negligible coloration on the fabrics being washed. Preferred amounts of the totality of the added colorants are below 1 wt. %, preferably below 0.1 wt. %, based on the composition. The compositions can also comprise white pigments such as e.g., $TiO_2$.

Food Compositions

Another embodiment of the present invention covers a food composition comprising a working amount of at least one acetophenone derivative or its mixtures with additional preservatives and/or antimicrobial agents, which might be present in amounts of from about 0.01 to about 10, preferably about 0.05 to about 5 and more preferably about 0.1 to about 1% b.w.—calculated on the total composition.

Food compositions according to the invention are any preparations or compositions which are suitable for consumption and are used for nutrition or enjoyment purposes, and are generally products which are intended to be introduced into the human or animal oral cavity, to remain there for a certain time and then either be eaten (e.g. ready-to-eat foodstuffs or feeds, see also herein below) or removed from the oral cavity again (e.g. chewing gums). Such products include any substances or products which in the processed, partially processed or unprocessed state are to be ingested by humans or animals. They also include substances which are added to orally consumable products during their manufacture, preparation or treatment and which are intended to be introduced into the human or animal oral cavity.

The food compositions according to the invention also include substances which in the unchanged, treated or prepared state are to be swallowed by a human or animal and then digested; in this respect, the orally consumable products according to the invention also include casings, coatings or other encapsulations which are to be swallowed at the same time or which may be expected to be swallowed. The expression "orally consumable product" covers ready-to-eat foodstuffs and feeds, that is to say foodstuffs or feeds that are already complete in terms of the substances that are important for the taste. The expressions "ready-to-eat foodstuff" and "ready-to-eat feed" also include drinks as well as solid or semi-solid ready-to-eat foodstuffs or feeds. Examples which may be mentioned are frozen products, which must be thawed and heated to eating temperature before they are eaten. Products such as yoghurt or ice-cream as well as chewing gums or hard caramels are also included among the ready-to-eat foodstuffs or feeds.

Preferred food compositions according to the invention also include "semi-finished products". Within the context of the present text, a semi-finished product is to be understood as being an orally consumable product which, because of a very high content of flavourings and taste-imparting substances, is unsuitable for use as a ready-to-eat orally consumable product (in particular foodstuff or feed). Only by mixing with at least one further constituent (e.g. by reducing the concentration of the flavourings and taste-imparting substances in question) and optionally further process steps (e.g. heating, freezing) is the semi-finished product converted into a ready-to-eat orally consumable product (in particular foodstuff or feed). Examples of semi-finished products which may be mentioned here are Food composition according to the invention preferably comprises one or more preparations for nutrition or enjoyment purposes. These include in particular (reduced-calorie) baked goods (e.g. bread, dry biscuits, cakes, other baked articles), confectionery (e.g. chocolates, chocolate bars, other products in bar form, fruit gums, dragées, hard and soft caramels, chewing gum), non-alcoholic drinks (e.g. cocoa, coffee, green tea, black tea, (green, black) tea drinks enriched with (green, black) tea extracts, rooibos tea, other herbal teas, fruit-containing soft drinks, isotonic drinks, refreshing drinks, nectars, fruit and vegetable juices, fruit or vegetable juice preparations), instant drinks (e.g. instant cocoa drinks, instant tea drinks, instant coffee drinks), meat products (e.g. ham, fresh sausage or raw sausage preparations, spiced or marinated fresh or salt meat products), eggs or egg products (dried egg, egg white, egg yolk), cereal products (e.g. breakfast cereals, muesli bars, precooked ready-to-eat rice products), dairy products (e.g. full-fat or reduced-fat or fat-free milk drinks, rice pudding, yoghurt, kefir, cream cheese, soft cheese, hard cheese, dried milk powder, whey, butter, buttermilk, partially or completely hydrolysed milk-protein-containing products), products made from soy protein or other soybean fractions (e.g. soy milk and products produced therefrom, drinks containing isolated or enzymatically treated soy protein, drinks containing soy flour, preparations containing soy lecithin, fermented products such as tofu or tempeh or products produced therefrom and mixtures with fruit preparations and optionally flavours), fruit preparations (e.g. jams, sorbets, fruit sauces, fruit fillings), vegetable preparations (e.g. ketchup, sauces, dried vegetables, frozen vegetables, precooked vegetables, boiled-down vegetables), snacks (e.g. baked or fried potato crisps or potato dough products, maize- or groundnut-based extrudates), fat- and oil-based products or emulsions thereof (e.g. mayonnaise, remoulade, dressings, in each case full-fat or reduced-fat), other ready-made dishes and soups (e.g. dried soups, instant soups, precooked soups), spices, spice mixtures and in particular seasonings which are used, for example, in the snacks field, sweetener preparations, tablets or sachets, other preparations for sweetening or whitening drinks or other foods. The preparations within the scope of the invention can also be used in the form of semi-finished products for the production of further preparations for nutrition or enjoyment purposes. The preparations within the scope of the invention can also be in the form of capsules, tablets (uncoated and coated tablets, e.g. enteric coatings), dragées, granules, pellets, solids mixtures, dispersions in liquid phases, in the form of emulsions, in the form of powders, in the form of solutions, in the form of pastes, or in the form of other preparations which can be swallowed or chewed, and in the form of food supplements.

The preparations can also be in the form of capsules, tablets (uncoated and coated tablets, e.g. enteric coatings), dragées, granules, pellets, solids mixtures, dispersions in liquid phases, in the form of emulsions, in the form of powders, in the form of solutions, in the form of pastes, or in the form of other preparations which can be swallowed or chewed, for example in the form of food supplements.

The semi-finished products are generally used for the production of ready-to-use or ready-to-eat preparations for nutrition or enjoyment purposes.

Further constituents of a ready-to-eat preparation or semi-finished product for nutrition or enjoyment purposes can be conventional base substances, auxiliary substances and additives for foods or enjoyment foods, for example water, mixtures of fresh or processed, vegetable or animal base or raw substances (e.g. raw, roast, dried, fermented, smoked and/or boiled meat, bone, cartilage, fish, vegetables, herbs, nuts, vegetable juices, vegetable pastes or mixtures thereof), digestible or non-digestible carbohydrates (e.g. sucrose, maltose, fructose, glucose, dextrins, amylose, amylopectin, inulin, xylans, cellulose, tagatose), sugar alcohols (e.g. sorbitol, erythritol), natural or hardened fats (e.g. tallow, lard, palm fat, cocoa fat, hardened vegetable fat), oils (e.g. sunflower oil, groundnut oil, maize germ oil, olive oil, fish oil, soya oil, sesame oil), fatty acids or their salts (e.g. potassium stearate), proteinogenic or non-proteinogenic amino acids and related compounds (e.g. γ-aminobutyric acid, taurine), peptides (e.g. glutathione), natural or processed proteins (e.g. gelatin), enzymes (e.g. peptidases), nucleic acids, nucleotides, taste correctors for unpleasant taste impressions, further taste modulators for further, generally not unpleasant taste impressions, other taste-modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum arabic), stabilisers (e.g. carrageenan, alginate), preservatives (e.g. benzoic acid and its salts, sorbic acid and its salts), antioxidants (e.g. tocopherol, ascorbic acid), chelators (e.g. citric acid), organic or inorganic acidifying agents (e.g. acetic acid, phosphoric acid), additional bitter substances (e.g. quinine, caffeine, limonene, amarogentine, humulone, lupulone, catechols, tannins), substances that prevent enzymatic browning (e.g. sulfite, ascorbic acid), ethereal oils, plant extracts, natural or synthetic colourings or colouring pigments (e.g. carotinoids, flavonoids, anthocyans, chlorophyll and derivatives thereof), spices, trigeminally active substances or plant extracts containing such trigeminally active substances, synthetic, natural or nature-identical flavourings or odorants as well as odour correctors.

Food compositions according to the invention, for example those in the form of preparations or semi-finished products, preferably comprise a flavour composition in order to complete and refine the taste and/or odour. A preparation can comprise as constituents a solid carrier and a flavour composition. Suitable flavour compositions comprise, for example, synthetic, natural or nature-identical flavourings, odorants and taste-imparting substances, reaction flavourings, smoke flavourings or other flavour-giving preparations (e.g. protein (partial) hydrolysates, preferably protein (partial) hydrolysates having a high arginine content, barbecue flavourings, plant extracts, spices, spice preparations, vegetables and/or vegetable preparations) as well as suitable auxiliary substances and carriers. Particularly suitable here are the flavour compositions or constituents thereof which produce a roasted, meaty (in particular chicken, fish, seafood, beef, pork, lamb, mutton, goat), vegetable-like (in particular tomato, onion, garlic, celery, leek, mushroom, aubergine, seaweed), spicy (in particular black and white pepper, cardamom, nutmeg, pimento, mustard and mustard products), fried, yeast-like, boiled, fatty, salty and/or pungent flavour impression and accordingly can enhance the spicy impression. The flavour compositions generally comprise more than one of the mentioned ingredients.

The food compositions of the present invention are preferably selected from the group comprising confectionery, preferably reduced-calorie or calorie-free confectionery, preferably selected from the group comprising muesli bar products, fruit gums, dragées, hard caramels and chewing gum, non-alcoholic drinks, preferably selected from the group comprising green tea, black tea, (green, black) tea drinks enriched with (green, black) tea extracts, rooibos tea, other herbal teas, fruit-containing low-sugar or sugar-free soft drinks, isotonic drinks, nectars, fruit and vegetable juices, fruit and vegetable juice preparations, instant drinks, preferably selected from the group comprising instant (green, black, rooibos, herbal) tea drinks, cereal products, preferably selected from the group comprising low-sugar and sugar-free breakfast cereals and muesli bars, dairy products, preferably selected from the group comprising reduced-fat and fat-free milk drinks, yoghurt, kefir, whey, buttermilk and ice-cream, products made from soy protein or other soybean fractions, preferably selected from the group comprising soy milk, products produced from soy milk, drinks containing isolated or enzymatically treated soy protein, drinks containing soy flour, preparations containing soy lecithin, products produced from preparations containing soy lecithin and mixtures with fruit preparations and optionally flavours, sweetener preparations, tablets and sachets, sugar-free dragées, ice-cream, with or without milk-based constituents, preferably sugar-free.

Aroma or Flavouring Compounds

Aroma compounds and flavouring agents (component d) are well known in the art can be added to the flavour compositions of the invention. These flavouring agents can be chosen from synthetic flavouring liquid and/or oils derived from plants leaves, flowers, fruits and so forth, and combinations thereof. Representative flavouring liquids include: artificial, natural or synthetic fruit flavours such as *eucalyptus*, lemon, orange, banana, grape, lime, apricot and grapefruit oils and fruit essences including apple, strawberry, cherry, orange, pineapple and so forth; bean and nut derived flavours such as coffee, cocoa, cola, peanut, almond and so forth; and root derived flavours such as licorice or ginger.

The flavouring agent is preferably selected from the group consisting of essential oils and extracts, tinctures and balsams, such as, for example, anisole, basil oil, bergamot oil, bitter almond oil, camphor oil, citronella oil, lemon oil; *Eucalyptus citriodora* oil, *eucalyptus* oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if the flavoured composition according to the invention comprises at least one flavouring agent, preferably two, three, four, five, six, seven, eight or more flavouring agents chosen from the following group: menthol (preferably l-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, transsabinene hydrate, menthofuran, caryophyllene, germacrene D, cinnamaldehyde, mint lactone, thymol, gamma-octalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

In particular preferred aroma or flavouring compounds encompass menthol, cineol, eugenol, thymol, cinnamic aldehyde, peppermint oil, spearmint oil, *eucalyptus* oil, thyme oil, cinnamon oil, clove oil, spruce needle oil, fennel oil, sage oil, aniseed oil, star anise oil, chamomile oil, and caraway oil, and their mixtures.

Sweetners

The term "sweeteners" here denotes substances having a relative sweetening power of at least 25, based on the sweetening power of sucrose (which accordingly has a sweetening power of 1). Sweeteners to be used in an orally consumable product (in particular foodstuff, feed or medicament) according to the invention (a) are preferably non-cariogenic and/or have an energy content of not more than 5 kcal per gram of the orally consumable product.

Advantageous sweeteners in a preferred food composition according to the invention are selected from the following groups:

Naturally occurring sweeteners, preferably selected from the group comprising
  miraculin, monellin, mabinlin, thaumatin, curculin, brazzein, pentaidin, D-phenylalanine, D-tryptophan, and extracts or fractions obtained from natural sources, comprising those amino acids and/or proteins, and the physiologically acceptable salts of those amino acids and/or proteins, in particular the sodium, potassium, calcium or ammonium salts;
  neohesperidin dihydrochalcone, naringin dihydrochalcone, stevioside, steviolbioside, rebaudiosides, in particular rebaudioside A, rebaudioside B, rebaudioside C, rebaudioside D, rebaudioside E, rebaudioside F, rebaudioside G, rebaudioside H, dulcosides and rubusoside, suavioside A, suavioside B, suavioside G, suavioside H, suavioside I, suavioside J, baiyunoside 1, baiyunoside 2, phlomisoside 1, phlomisoside 2, phlomisoside 3 and phlomisoside 4, abrusoside A, abrusoside B, abrusoside C, abrusoside D, cyclocaryoside A and cyclocaryoside I, osladin, polypodoside A, strogin 1, strogin 2, strogin 4, selligueain A, dihydroquercetin 3-acetate, perillartin, telosmoside $A_{15}$, periandrin I-V, pterocaryosides, cyclocaryosides, mukuroziocides, trans-anethole, trans-cinnamaldehyde, bryosides, bryonosides, bryonodulcosides, carnosiflosides, scandenosides, gypenosides, trilobatin, phloridzin, dihydroflavanols, hematoxylin, cyanin, chlorogenic acid, albiziasaponin, telosmosides, gaudichaudioside, mogrosides, mogroside V, hernandulcins, monatin, phyllodulcin, glycyrrhetinic acid and derivatives thereof, in particular glycosides thereof such as glycyrrhizine, and the physiologically acceptable salts of those compounds, in particular the sodium, potassium, calcium or ammonium salts;
  extracts or concentrated fractions of the extracts, selected from the group comprising *thaumatococcus* extracts (katamfe plant), extracts from *Stevia* ssp. (in particular *Stevia rebaudiana*), swingle extracts (*Momordica* or *Siratia grosvenorii*, Luo-Han-Guo), extracts from *Glycerrhyzia* ssp. (in particular *Glycerrhyzia glabra*), extracts from *Rubus* ssp. (in particular *Rubus suavissimus*), citrus extracts and extracts from *Lippia dulcis;*

Synthetic sweet-tasting substances, preferably selected from the group comprising magap, sodium cyclamate or other physiologically acceptable salts of cyclamic acid, acesulfame K or other physiologically acceptable salts of acesulfame, neohesperidin dihydrochalcone, naringin dihydrochalcone, saccharin, saccharin sodium salt, aspartame, superaspartame, neotame, alitame, advantame, perillartin, sucralose, lugduname, carrelame, sucrononate and sucrooctate.

Thickeners

Advantageous thickeners in a preferred orally consumable product (in particular foodstuff, feed or medicament) according to the invention are selected from the group comprising: crosslinked polyacrylic acids and derivatives thereof, polysaccharides and derivatives thereof, such as xanthan gum, agar-agar, alginates or tyloses, cellulose derivatives, for example carboxymethylcellulose or hydroxycarboxymethylcellulose, fatty alcohols, monoglycerides and fatty acids, polyvinyl alcohol and polyvinylpyrrolidone.

Preference is given according to the invention to an orally consumable product (in particular foodstuff or feed) which comprises milk thickened with lactic acid bacteria and/or cream thickened with lactic acid bacteria and which preferably is selected from the group comprising yoghurt, kefir and quark.

A food composition according to the invention comprising milk thickened with lactic acid bacteria and/or cream thickened with lactic acid bacteria is advantageously an orally consumable product which comprises a probiotic, wherein the probiotic is preferably selected from the group comprising *Bifidobacterium animalis* subsp. *lactis* BB-12, *Bifidobacterium animalis* subsp. *lactis* DN-173 010, *Bifidobacterium animalis* subsp. *lactis* HN019, *Lactobacillus acidophilus* LA5, *Lactobacillus acidophilus* NCFM, *Lactobacillus johnsonii* La1, *Lactobacillus casei* immunitass/defensis, *Lactobacillus casei* Shirota (DSM 20312), *Lactobacillus casei* CRL431, *Lactobacillus reuteri* (ATCC 55730) and *Lactobacillus rhamnosus* (ATCC 53013).

Additives for Chewing Gums

Particular preference is given to an orally consumable product (in particular foodstuff, feed or medicament) according to the invention that is a chewing gum and comprises a chewing-gum base. The chewing-gum base is preferably selected from the group comprising chewing-gum or bubble-gum bases. The latter are softer, so that gum bubbles can also be formed therewith. Preferred chewing-gum bases according to the invention include, in addition to the natural resins or the natural latex chicle that are traditionally used, elastomers such as polyvinyl acetate (PVA), polyethylene, (low or medium molecular weight) polyisobutene (PIB), polybutadiene, isobutene-isoprene copolymers (butyl rubber), polyvinyethyl ether (PVE), polyvinylbutyl ether, copolymers of vinyl esters and vinyl ethers, styrene-butadiene copolymers (styrene-butadiene rubber, SBR) or vinyl elastomers, for example based on vinyl acetate/vinyl laurate, vinyl acetate/vinyl stearate or ethylene/vinyl acetate, as well as mixtures of the mentioned elastomers, as described, for example, in EP 0 242 325, U.S. Pat. Nos. 4,518,615, 5,093,136, 5,266,336, 5,601,858 or 6,986,709. In addition, chewing-gum bases that are preferably to be used according to the invention preferably comprise further constituents such as, for example, (mineral) fillers, plasticisers, emulsifiers, antioxidants, waxes, fats or fatty oils, such as, for example, hardened (hydrogenated) vegetable or animal fats, mono-, di- or tri-glycerides. Suitable (mineral) fillers are, for example, calcium carbonate, titanium dioxide, silicon dioxide, talcum, aluminum oxide, dicalcium phosphate, tricalcium phosphate, magnesium hydroxide and mixtures thereof. Suitable plasticisers, or agents for preventing adhesion (detackifiers), are, for example, lanolin, stearic acid, sodium stearate, ethyl acetate, diacetin (glycerol diacetate), triacetin (glycerol triacetate), triethyl citrate. Suitable waxes are, for example, paraffin waxes, candelilla wax, carnauba wax, microcrystalline waxes and polyethylene waxes. Suitable emulsifiers are, example, phosphatides such as lecithin, mono- and di-glycerides of fatty acids, for example glycerol monostearate.

Chewing gums according to the invention (in particular as disclosed above) preferably comprise constituents such as sugars of different types, sugar substitutes, other sweet-tasting substances, sugar alcohols (in particular sorbitol, xylitol, mannitol), ingredients having a cooling effect, taste correctors for unpleasant taste impressions, further taste-modulating substances (e.g. inositol phosphate, nucleotides such as guanosine monophosphate, adenosine monophosphate or other substances such as sodium glutamate or 2-phenoxypropionic acid), humectants, thickeners, emulsifiers, stabilisers, odour correctors and flavours (e.g. *eucalyptus*-menthol, cherry, strawberry, grapefruit, vanilla, banana, citrus, peach, blackcurrant, tropical fruits, ginger, coffee, cinnamon, combinations (of the mentioned flavours) with mint flavours as well as spearmint and peppermint on their own). The combination inter alia of the flavours with further substances that have cooling, warming and/or mouth-watering properties is of particular interest.

Methods for Preservation and Fighting Body Odor

The acetophenone derivatives and the respective mixtures according to the invention display their synergistically intensified antimicrobial action against a large number of Gram-positive bacteria, Gram-negative bacteria, moulds and yeasts, which in particular renders possible preservation and antimicrobial treatment of a large number of cosmetic formulations. A particularly good action exists against Gram-positive bacteria, such as *Staphylococcus aureus, Staphylococcus epidermidis, Corynebacterium xerosis,* and *Propionibacterium acnes*, against Gram-negative bacteria, such as *Escherichia coli* and *Pseudomonas aeruginosa*, against yeasts, such as *Candida albicans, Malassezia furfur* and *globosa*, and precisely—as already mentioned—against fungi, such as mould species of the genus *Aspergillus* and others. The very good activity of the mixtures according to the invention against moulds of the genus *Aspergillus*, a fungal group, which can be combated only with great difficulty, is to be regarded as particularly advantageous here.

Therefore, another object of the present invention relates to a method for preserving a personal care composition, a detergent composition or a food composition by adding a working amount of at least one acetophenone derivative or its mixture with a second preservative or an antimicrobial agent.

Another object of the present invention refers to a method for fighting microorganisms by adding a working amount of at least one acetophenone derivative or its mixture with a second preservative or an antimicrobial agent to a personal care, detergent or food composition.

The invention covers also the use of at least one acetophenone derivative or its mixture with a second preservative or an antimicrobial agent as a preservative, in particular for personal care, detergent or food compositions, preferably in amounts of from about 0.01 to about 10, preferably about 0.05 to about 5 and more preferably about 0.1 to about 1% b.w.

Another object of the present invention refers to a method for fighting microorganisms by adding a working amount of at least one acetophenone derivative or its mixture with a second preservative or an antimicrobial agent.

The acetophenone derivatives and their mixtures are particularly useful against microorganisms which cause body odour, acne and/or mycoses. Advantageously, the preservatives or preservative mixtures are applied to human skin at concentrations of 0.01 to about 10, preferably about 0.05 to about 5 and more preferably about 0.1 to about 1% b.w. in each case based on the total weight of the cosmetic or pharmaceutical product which comprises the mixture. The synergistically active mixtures can be employed here (a) prophylactically or (b) as required. The concentration of the amount of active compound to be applied e.g. daily varies and depends on the physiological state of the subject and individual-specific parameters, such as age or body weight. The synergistically active mixtures according to the invention can be employed either by themselves or in combination with further antimicrobically active substances.

Another object of the present invention therefore covers a method for treating unpleasant body odour, in particular underarm and foot odour by topical administration a working amount of at least one acetophenone derivative or its mixture with a second preservative or an antimicrobial agent to the skin. Finally, the invention refers to the use of at least one acetophenone derivative or its mixture with a second preservative or an antimicrobial as a deodorant.

It is understood that the explanations and preferred embodiments outlined above with respect to the acetophenone derivatives and their mixtures mutatis-mutandis apply also for the methods and uses as claimed, thus no additional repetition is necessary.

EXAMPLES

Example 1

Synergistic Activity of 4-hydroxyacetophenone and Phenoxyethanol Against the Microorganism *A. Brasiliensis*

To calculate the synergism between compounds of formula (I) and other antimicrobial actives, the Kull equation[1], [2] was used $$SI = (C_{mixture} \times P_A)/C_A + (C_{mixture} \times P_B)/C_B \quad (I)$$

where

SI is the Synergy Index according to Kull[1], [2]

$C_A$ is the cell count for substance A $C_B$ is the cell count for substance B $C_{mixture}$ is the cell count for the mixture of substances A and B $P_A$ is the proportion of the substance A in the mixture $P_B$ is the proportion of the substance B in the mixture.

Colony counts of <100 were arbitrarily set to 100, in order to allow for synergy calculations with the above equation. The results for 4-hydroxyacetophenone (4HAP) and phenoxyethanol (POE) are shown in Table 1. The abbreviation "n.a." means not applicable.

TABLE 1

| Synergistic activity of 4-hydroxyacetophenone and phenoxyethanol | | | | | |
|---|---|---|---|---|---|
| | day 0 | day 2 | day 7 | day 14 | day 28 |
| | Colony counts (cfu/g formulation) | | | | |
| 1.0% 4HAP | 300.000 | 56.000 | 1.900 | 1.900 | <100 |
| 1.0% POE | 237.000 | 211.000 | 34.000 | 10.000 | <100 |
| 0.5% 4HAP + 0.5% POE | 160.000 | 17.000 | <100 | <100 | 0 |

TABLE 1-continued

Synergistic activity of 4-hydroxyacetophenone and phenoxyethanol

|  | day 0 | day 2 | day 7 | day 14 | day 28 |
|---|---|---|---|---|---|
|  | Relative colony counts | | | | |
| 1.0% 4HAP | 1.0000 | 0.1867 | 0.0063 | 0.0063 | 0.0003 |
| 1.0% POE | 1.0000 | 0.8915 | 0.1438 | 0.0401 | 0.0003 |
| 0.5% 44HAP + 0.5% POE | 1.0000 | 0.1063 | 0.0006 | 0.0006 | 0.0000 |
| Synergy Index SI | n.a. | 0.344 | 0.0515 | 0.0571 | <0.0001 |

The Synergy Index SI for the combination of 4-hydroxyacetophenone and Phenoxyethanol against *A. brasiliensis*, calculated according to Kull's equation (I), is 0.344, 0,052, 0,057, and <0,0001 for the time points day 2, 7, 14, and 28, respectively, indicating a very strong synergism between these two compounds.

[1] Kull, F. C., Eismann, P. C., Sylvestrowicz, H. D., and R. L. Mayer (1961). Mixtures of Quaternary Ammonium Compounds and Long-chain Fatty Acids as Antifungal Agents. Applied Microbiology 9, 538-541.

[2] Steinberg, D. C. (2000). Measuring Synergy. Cosmetics & Toiletries 115 (11), 59-62.

Example 2

The synergistic activity of 4-hydroxyacetophenone (4HAP) and ethylhexyl glycerin (EHG) against the microorganism *A. brasiliensis* was determined. The results are shown in Table 2.

TABLE 2

Synergistic activity of 4-hydroxyacetophenone and ethylhexyl glycerin

|  | day 0 | day 2 | day 7 | day 14 | day 28 |
|---|---|---|---|---|---|
|  | Colony counts (cfu/g formulation) | | | | |
| 1.0% 4HAP | 300.000 | 56.000 | 1.900 | 1.900 | <100 |
| 1.0% EHG | 315.000 | 159.000 | 150.000 | 304.000 | 304.000 |
| 0.3% 4HAP + 0.7% EHG | 380.000 | 0 | 0 | 0 | 0 |
|  | Relative colony counts | | | | |
| 1.0% 4HAP | 1.0000 | 0.1867 | 0.0063 | 0.0063 | 0.0003 |
| 1.0% EHG | 0.5048 | 0.4762 | 0.9635 | 0.9635 | 0.5048 |
| 0.3% 4HAP + 0.7% EHG | 1.0000 | 0.0000 | 0.0000 | 0.0000 | 0.0000 |
| Synergy Index SI | n.a. | <0.0001 | <0.0001 | <0.0001 | <0.0001 |

The Synergy Index SI for the combination of 4-hydroxyacetophenone and Ethylhexyl glycerin against *A. brasiliensis*, calculated according to Kull's equation (I), is <0.0001 for the time points day 2, 7, 14, and 28, respectively, indicating a very strong synergism between these two compounds.

Example 3

The synergistic activity of 4-hydroxyacetophenone (4HAP) and 3-heptyloxy-1,2-propanediol (3HOPD) against the microorganism *A. brasiliensis* was determined. The results are shown in Table 3.

TABLE 3

Synergistic activity of 4-hydroxyacetophenone and 3-heptyloxy-1,2-propanediol

|  | day 0 | day 2 | day 7 | day 14 | day 28 |
|---|---|---|---|---|---|
| Colony counts (cfu/g formulation) | | | | | |
| 1.0% 4HAP | 300.000 | 56.000 | 1.900 | 1.900 | <100 |
| 1.0% 3HOPD | 220.000 | 320.000 | 340.000 | 300.000 | 170.000 |
| 0.3% 4HAP + 0.7% 3HOPD | 220.000 | 6.800 | <100 | 0 | 0 |
| Relative colony counts | | | | | |
| 1.0% 4HAP | 1.0000 | 0.1867 | 0.0063 | 0.0063 | 0.0003 |
| 1.0% 3HOPD | 1.0000 | 1.4545 | 1.5455 | 1.3636 | 0.7727 |
| 0.3% 4HAP + 0.7% 3HOPD | 1.0000 | 0.0309 | 0.0005 | 0.0000 | 0.0000 |
| Synergy Index SI | n.a.[1] | 0.0309 | 0.0005 | <0.0001 | <0.0001 |

The Synergy Index SI for the combination of 4-hydroxyacetophenone and 3-heptyloxy-1,2-propanediol against *A. brasiliensis*, calculated according to Kull's equation (I), is 0.0309, 0,0005, <0,0001, and <0,0001 for the time points day 2, 7, 14, and 28, respectively, indicating a very strong synergism between these two compounds.

Example 4

The synergistic activity of 4-hydroxyacetophenone (4HAP) and 1,2-Hexanediol (HD), against the microorganism *A. brasiliensis* was determined. The results are shown in Table 4:

TABLE 4

Synergistic activity of 4-hydroxyacetophenone and 1,2-Hexanediol

|  | day 0 | day 2 | day 7 | day 14 | day 28 |
|---|---|---|---|---|---|
| Colony counts (cfu/g formulation) | | | | | |
| 1.0% 4HAP | 300.000 | 56.000 | 1.900 | 1.900 | <100 |
| 3.0% HD | 305.000 | 306.000 | 266.000 | 96.000 | <100 |
| 0.5% 4HAP 0.5% HD | 200.000 | 88.000 | <100 | <100 | <100 |
| Relative colony counts | | | | | |
| 1.0% 4HAP | 1.0000 | 0.1867 | 0.0063 | 0.0063 | 0.0003 |
| 3.0% HD | 1.0000 | 1.0033 | 0.8721 | 0.3148 | 0.0003 |
| 0.5% 4HAP + 0.5% HD | 1.0000 | 0.4400 | 0.0005 | 0.0005 | 0.0005 |
| Synergy Index SI | n.a. | 1.2518 | 0.0396 | 0.0397 | 1.0047[1] |

([1]all values below detection limit)

The Synergy Index SI for the combination of 4-hydroxyacetophenone and 1,2-Hexanediol against *A. brasiliensis*, calculated according to Kull's equation (I), is 1.2518, 0,0396, 0,0397, and 1,0047 for the time points day 2, 7, 14, and 28, respectively, indicating a very strong synergism between these two compounds for day 7 and day 14. A synergistic activity at day 28 could not be observed, since all values were below detection limit.

Example 5

The synergistic activity of 4-hydroxyacetophenone (4HAP) and further antimicrobial agents against the microorganisms *Staphylococcus aureus*, *Candida albicans*, *Aspergillus brasiliensis*, *Pseudomonas aeruginosa* and *Escherichia coli* were determined by measuring minimum inhibitory concentrations (MIC values) according to DIN 58940. The results are shown in Tables 5, 6 and 7:

In order to calculate the Synergy Index SI with MIC values, the Kull equation is used as follows:

Mixtures Containing 2 Components:

$$SI = (MIC_{mixture} \times P_A)/MIC_A + (MIC_{mixture} \times P_B)/MIC_B \quad (II)$$

where
SI is the Synergy Index according to Kull[1, 2]
$MIC_A$ is the MIC value for substance A
$MIC_B$ is the MIC value for substance B
$MIC_{mixture}$ is the MIC value for the mixture of substances A and B
$P_A$ is the proportion of the substance A in the mixture
$P_B$ is the proportion of the substance B in the mixture.

Mixtures Containing 3 Components:

$$SI = (MIC_{mixture} \times P_A)/MIC_A + (MIC_{mixture} \times P_B)/MIC_B + (MIC_{mixture} \times P_C)/MIC_C \quad (III)$$

where
SI is the Synergy Index according to Kull[1, 2]
$MIC_A$ is the MIC value for substance A
$MIC_B$ is the MIC value for substance B
$MIC_C$ is the MIC value for substance C
$MIC_{mixture}$ is the MIC value for the mixture of substances A and B
$P_A$ is the proportion of the substance A in the mixture
$P_B$ is the proportion of the substance B in the mixture.
$P_C$ is the proportion of the substance C in the mixture.

Mixtures Containing 4 Components:

$$SI = (MIC_{mixture} \times P_A)/MIC_A + (MIC_{mixture} \times P_B)/MIC_B + (MIC_{mixture} \times P_C)/MIC_C + (MIC_{mixture} \times P_D)/MIC_D \quad (IV)$$

where
SI is the Synergy Index according to Kull[1, 2]
$MIC_A$ is the MIC value for substance A
$MIC_B$ is the MIC value for substance B $MIC_C$ is the MIC value for substance C
$MIC_D$ is the MIC value for substance D
$MIC_{mixture}$ is the MIC value for the mixture of substances A and B
$P_A$ is the proportion of the substance A in the mixture
$P_B$ is the proportion of the substance B in the mixture.
$P_C$ is the proportion of the substance C in the mixture.
$P_D$ is the proportion of the substance D in the mixture.

TABLE 5

Minimum inhibitory concentrations of different antimicrobial agents

| Substance name | CAS number | MIC values (ppm) | | | | |
| --- | --- | --- | --- | --- | --- | --- |
| | | Staphylococcus aureus | Candida albicans | Aspergillus brasiliensis | Pseudomonas aeruginosa | Escherichia coli |
| 4HAP | 99-93-4 | 6000 | 6000 | 4000 | 4000 | 4000 |
| 1,3-Propanediol | 504-63-2 | 125000 | 100000 | 150000 | 100000 | 100000 |
| Phenoxyethanol | 122-99-6 | 5000 | 10000 | 2000 | 2500 | 5000 |
| 3-Phenylpropanol | 122-97-4 | 2000 | 5000 | 2000 | 2000 | 2000 |
| 1,2-Hexanediol | 6920-22-5 | 20000 | 20000 | 10000 | 10000 | 10000 |
| 1,2-Octanediol | 1117-86-8 | 5000 | 5000 | 1000 | 5000 | 2500 |
| Ethylhexylglycerin | 1117-86-8 | 2000 | 2000 | 2000 | >20000 | 2500 |
| Hexylglycerin | 208402-97-5 | 6000 | 6000 | 4000 | 6000 | 4000 |
| Heptylglycerin | 208402-98-6 | 2500 | 2000 | 1000 | 5000 | 2000 |
| Octylglycerin | 127641-38-7 | 1000 | 1000 | 500 | >2000 | 1000 |
| Benzylglycerin | 4799-67-1 | 20000 | 20000 | 20000 | 20000 | 10000 |

TABLE 6

Minimum inhibitory concentrations of mixtures of 4-hydroxyacetophenone with different antimicrobial agents

| Mixtures | Ratio | MIC values (ppm) | | | | |
| --- | --- | --- | --- | --- | --- | --- |
| | | Staphylococcus aureus | Candida albicans | Aspergillus brasiliensis | Pseudomonas aeruginosa | Escherichia coli |
| 4HAP/Phenoxyethanol | 3:7 | 4000 | 6000 | 4000 | 4000 | 4000 |
| 4HAP/Phenoxyethanol | 1:1 | 4000 | 8000 | 4000 | 4000 | 4000 |
| 4HAP/1,2-Hexanediol/1,3-Propanediol | 1:1:2 | 20000 | 20000 | 10000 | 6000 | 8000 |
| 4HAP/3-Phenylpropanol/Ethylhexylglycerin/1,3-Propanediol | 5:4:1:10 | 6000 | 8000 | 4000 | 4000 | n.d. |
| 4HAP/Phenoxyethanol/1,2-Hexanediol | 3:4:3 | 6000 | 6000 | 4000 | 4000 | 4000 |
| 4HAP/Phenoxyethanol/1,2-Hexanediol/1,2-Octanediol | 6:8:3:3 | 4000 | 4000 | 4000 | 4000 | 4000 |
| 4HAP/Phenoxyethanol/Hexylglycerin | 5:10:5 | 4000 | 6000 | 4000 | 4000 | 4000 |
| 4HAP/Phenoxyethanol/Heptylglycerin | 5:10:5 | 4000 | 4000 | 2000 | 4000 | 4000 |
| 4HAP/Phenoxyethanol/Octylglycerin | 5:10:5 | 2000 | 4000 | 1000 | 4000 | 2000 |
| 4HAP/Phenoxyethanol/Benzylglycerin | 5:10:5 | 6000 | 6000 | 4000 | 4000 | 4000 |
| 4HAP/Ethylhexylglycerin | 3:7 | 2000 | 2000 | 2000 | >4000 | n.d. |
| 4HAP/Heptylglycerin | 3:7 | 2000 | 2000 | 1000 | 4000 | 2000 |
| 4HAP/1,2-Hexanediol/1,2-Octanediol/1,3-Propanediol | 2:1:1:4 | 6000 | 8000 | 6000 | 6000 | 6000 |
| 4HAP/3-Phenylpropanol/1,2-Octanediol/1,3-Propanediol | 2:1:1:4 | 6000 | 8000 | 4000 | 6000 | n.d. | n.d. = not determined

TABLE 7

Synergy Index SI of mixtures of 4-hydroxyacetophenone with different antimicrobial agents.

| Mixtures | Ratio | Staphylococcus aureus | Candida albicans | Aspergillus brasiliensis | Pseudomonas aeruginosa | Escherichia coli |
|---|---|---|---|---|---|---|
| 4-HAP/Phenoxyethanol | 3:7 | 0,76 | 0,72 | n.s. | n.s. | 0,86 |
| 4-HAP/Phenoxyethanol | 1:1 | 0,733 | n.s. | n.s. | n.s. | 0,9 |
| 4-HAP/1,2-Hexanediol/1,3-Propanediol | 1:1:2 | n.s. | n.s. | 0,908 | 0,555 | 0,74 |
| 4-HAP/3-Phenylpropanol/Ethylhexylglycerin/1,3-Propanediol | 5:4:1:10 | n.s. | 0,893 | 0,763 | n.s. | |
| 4-HAP/Phenoxyethanol/1,2-Hexanediol | 3:4:3 | 0,87 | 0,63 | n.s. | n.s. | 0,65 |
| 4-HAP/Phenoxyethanol/1,2-Hexanediol/1,2-Octanediol | 6:8:3:3 | 0,67 | 0,51 | n.s. | n.s. | 0,92 |
| 4-HAP/Phenoxyethanol/Hexylglycerin | 5:10:5 | 0,733 | 0,8 | n.s. | n.s. | 0,9 |
| 4-HAP/Phenoxyethanol/Heptylglycerin | 5:10:5 | 0,967 | 0,867 | n.s. | n.s. | n.s. |
| 4-HAP/Phenoxyethanol/Octylglycerin | 5:10:5 | 0,783 | n.s. | 0,813 | n.d. | 0,825 |
| 4-HAP/Phenoxyethanol/Benzylglycerin | 5:10:5 | 0,925 | 0,625 | n.s. | n.s. | 0,75 |
| 4-HAP/Ethylhexylglycerin | 3:7 | 0,8 | 0,8 | 0,85 | n.d. | |
| 4-HAP/Heptylglycerin | 3:7 | 0,66 | 0,8 | 0,775 | 0,86 | 0,85 |
| 4-HAP/1,2-Hexanediol/1,2-Octanediol/1,3-Propanediol | 2:1:1:4 | 0,462 | 0,623 | n.s. | 0,63 | 0,78 |
| 4-HAP/3-Phenylpropanol/1,2-Octanediol/1,3-Propanediol | 2:1:1:4 | 0,799 | 0,773 | n.s. | 0,93 | | n.s. = not synergistic;
n.d. = not determined

The Synergy Index SI for the combination of 4-hydroxyacetophenone with different antimicrobial agents against *Staphylococcus aureus*, *Candida albicans*, *Aspergillus brasiliensis*, *Pseudomonas aeruginosa* and *Escherichia coli*, calculated according to Kull's equation (II), (III), and (IV), is below 1 in many cases, indicating a synergism between 4-hydroxyacetophenone and different antimicrobial agents.

FORMULATION EXAMPLES

The present invention is further illustrated by the following examples. If not indicated otherwise a reference to a "substance of formula (I)" relates to 4-hydroxyacetophenone (compound of formula (IIc)). However, the "substance of formula (I)" can be replaced by any other compound of formula (I). In particular 4-hydroxyacetophenone can be replaced by 2-hydroxyacetophenone (compound of formula (IIa)), or 3-hydroxyacetophenone (compound of formula (IIb)).

TABLE IA

Perfume oil P1 (Amounts in % b.w.)

| Ingredients | Amount |
|---|---|
| AMBRETTOLIDE (MACRO) | 10.00 |
| AMBROXIDE 10% in IPM | 10.00 |
| BENZYL ACETATE | 20.00 |
| BENZYL SALICYLATE | 15.00 |
| BERGAMOT OIL. bergapten-free | 60.00 |
| CALONE ® 1951 10% in DPG | 15.00 |
| COUMARIN | 5.00 |
| CYCLOGALBANATE ® 10% in DPG | 10.00 |
| ALPHA -DAMASCONE 1% in DPG | 20.00 |
| DIHYDROMYRCENOL | 10.00 |
| ETHYL LINALOOL | 75.00 |

TABLE IA-continued

Perfume oil P1 (Amounts in % b.w.)

| Ingredients | Amount |
|---|---|
| ETHYL LINALYLACETATE | 50.00 |
| ETHYL MALTOL 1% in DEP | 10.00 |
| ETHYLENE BRASSYLATE (MACRO) | 80.00 |
| FLOROSA | 40.00 |
| GERANYLACETATE | 10.00 |
| HEDIONE ® HC/30 | 35.00 |
| HEDIONE ® | 210.00 |
| HELIONAL ® | 15.00 |
| HELVETOLIDE ® (ALICYC) | 30.00 |
| HEXENYLSALICYLATE CIS-3 | 20.00 |
| ISO E SUPER ® | 40.00 |
| LEAFOVERT 10% in DEP | 10.00 |
| LILIAL ® | 80.00 |
| LYRAL ® | 20.00 |
| MANDARIN OIL | 10.00 |
| STYRALYL ACETATE | 5.00 |
| SYMROSE ® | 15.00 |
| VANILLIN 10% in DEP | 20.00 |
| DIPROPYLENE GLYCOL (DPG) | 50.00 |
| TOTAL: | 1,000.00 |

TABLE IB

Perfume oil P2 (Amounts in % b.w.)

| Ingredients | Amount |
|---|---|
| AMAROCITE ® | 10.00 |
| AMBROCENIDE ® 10% in DPG | 5.00 |
| AMBROXIDE | 15.00 |
| AURELIONE ® (7/8-Cyclohexadecenone) (MACRO) | 70.00 |
| BERGAMOT OIL bergapten-free | 90.00 |

TABLE IB-continued

Perfume oil P2 (Amounts in % b.w.)

| Ingredients | Amount |
|---|---|
| CALONE ® 1951 10% in DPG | 20.00 |
| CARAWAY OIL | 10.00 |
| CITRAL | 20.00 |
| COUMARIN | 10.00 |
| ALPHA-DAMASCONE 1% in DPG | 15.00 |
| DIHYDROMYRCENOL | 70.00 |
| ESTRAGON OIL | 10.00 |
| ETHYL LINALOOL | 100.00 |
| ETHYL LINALYLACETATE | 90.00 |
| EUGENOL | 10.00 |
| EVERNYL ® | 5.00 |
| FRUCTATE ® | 5.00 |
| GERANIUM OIL | 5.00 |
| HEDIONE ® HC/30 | 100.00 |
| HELIONAL ® | 10.00 |
| INDOLE 10% in DPG | 5.00 |
| ISO E SUPER ® | 100.00 |
| KEPHALIS ® | 5.00 |
| LAVENDER OIL | 40.00 |
| CITRUS OIL | 80.00 |
| LILIAL ® | 30.00 |
| MANDARIN OIL | 20.00 |
| MUSCENONE (MACRO) | 5.00 |
| SANDRANOL ® | 10.00 |
| VANILLIN 10% in DPG | 5.00 |
| DIPROPYLENE GLYCOL | 30.00 |
| TOTAL: | 1,000.00 |

TABLE IC

Perfume oil P3 (Amounts in % b.w.)

| Ingredients | Amount |
|---|---|
| ALDEHYDE C10 (n-decanal) 10% in DPG | 20.00 |
| ALDEHYDE C11 (n-undecanal) 10% in DPG | 5.00 |
| ALDEHYDE C12 (n-dodecanal) 10% in DPG | 15.00 |
| AMBRETTOLIDE (MACRO) | 5.00 |
| AMBROCENIDE ® 1% in DPG | 20.00 |
| AURELIONE ® (MACRO) | 30.00 |
| BENZYL ACETATE | 30.00 |
| CITRONELLA OIL | 15.00 |
| ETHYL VANILLIN 1% in DPG | 20.00 |
| ETHYLENE BRASSYLATE (MACRO) | 70.00 |
| FRUCTATE ® 10% in DPG | 20.00 |
| GERANYL ACETATE | 10.00 |
| GLOBALIDE ® (MACRO) | 30.00 |

TABLE IC-continued

Perfume oil P3 (Amounts in % b.w.)

| Ingredients | Amount |
|---|---|
| HEDIONE ® | 30.00 |
| ALPHA-HEXYLCINNAMALDEHYDE | 90.00 |
| INDOLE 10% in DPG | 5.00 |
| ISO E SUPER ® | 120.00 |
| KEPHALIS ® | 5.00 |
| LINALOOL | 150.00 |
| LINALYL ACETATE | 60.00 |
| BETA-METHYLNAPHTYLKETONE | 5.00 |
| NEROLIDOL | 20.00 |
| NEROLIONE 10% in DPG | 20.00 |
| BRAZILIAN ORANGE OIL | 100.00 |
| PHENYLETHYL ACETATE | 5.00 |
| PHENYLETHYL ALCOHOL | 30.00 |
| TERPINEOL | 20.00 |
| DIPROPYLENE GLYCOL | 50.00 |
| TOTAL: | 1,000.00 |

TABLE ID

Perfume oil P4 with white blossom smell (Amounts in % b.w.)

| Ingredients | Amount |
|---|---|
| Benzylacetate | 60.00 |
| Citronellylacetate | 60.00 |
| Cyclamene aldehyde (2-methyl-3-(4-isopropylphenyl)propanal | 20.00 |
| Dipropylene glycol | 60.00 |
| Ethyllinalool | 40.00 |
| Florol (2-isobutyl-4-methyltetrahydro-2H-pyran-4-ol) | 30.00 |
| Globanone [(E/Z)-8-cyclohexadecen-1-one] | 180.00 |
| Hedione (methyldihydrojasmonate) | 140.00 |
| Hexenylsalicylate. cis-3 | 10.00 |
| Vertocitral (2.4-dimethyl-3-cyclohexenecarboxaldehyde) | 5.00 |
| Hydratropaaldehyde. 10% in DPG | 5.00 |
| Isodamascone (1-(2.4.4-trimethyl-2-cyclohexen-1-yl)-2-buten-1-one. 10% in DPG | 5.00 |
| Isomuscone (cyclohexadecanone) | 40.00 |
| Jacinthaflor (2-methyl-4-phenyl-1.3-dioxolane) | 10.00 |
| Cis-jasmone. 10% in DPG | 20.00 |
| Linalool | 50.00 |
| Linalylacetate | 30.00 |
| Methylbenzoate. 10% in DPG | 25.00 |
| para-methyl cresol. 10% in DPG | 10.00 |
| Nerol | 20.00 |
| Phenylpropylaldehyde | 5.00 |
| 2-Phenylethyl alcohol | 82.00 |
| Tetrahydrogeraniol | 13.00 |
| 2.2-dimethyl-3-cyclohexyl-1-propanol | 80.00 |
| Total: | 1,000.00 |

The perfume oils P1, P2, P3, and P4 from the above examples were worked separately in each case into the here presented formulations.

TABLE II

Liquid soap, transparent (Amounts in % b.w.)

| Ingredients | INCI Name | Amount |
| --- | --- | --- |
| Tagat O 2 | PEG-20 Glyceryl Oleate | 2.5 |
| Coconut oil diethanolamine condensate | Cocamide DEA | 5.0 |
| Abil B 8842 | Cyclomethicone | 0.5 |
| Sodium laurylethersulfate. 28% | Sodium Laureth Sulfate | 35.0 |
| Tego-Betaine L7 | Cocamidopropyl Betaine | 5.0 |
| Soap. 25% | Coconut acid. Potassium salt. Potassium Oleate | 20.0 |
| Perfume oil P1. P2. P3 or P4 | Fragrance | 0.4 |
| Preservative | DMDM Hydantoin | 0.2 |
| Substance of formula (I) | Hydroxyacetophenone | 0.3 |
| Water | Water | Ad 100 |

TABLE III

Syndet soap. liquid (Amounts in % b.w.)

| Ingredients | INCI Name | Amount |
| --- | --- | --- |
| Elfan OS 46 | Sodium Olefin C14-C16 Sulfonate | 35.5 |
| Armoteric LB | Lauryl Betaine | 8.0 |
| Elfan SG | | 10.0 |
| Elfacos GT 282 L | Talloweth-60 Myristyl Glycol | 3.0 |
| PCL-Liquid 100 | Cetearyl Ethylhexanoate | 4.0 |
| Perfume oil P1. P2. P3 or P4 | Fragrance | 0.4 |
| Preservative | Methylchloroisothiazolinone. Methyl-isothiazinone | 0.1 |
| Substance of formula (I) | Hydroxyacetophenone | 0.4 |
| Water | Water | Ad 100 |

TABLE IV

Cosmetic lotion for body wash (Amounts in % b.w.)

| Ingredients | INCI Name | Amount |
| --- | --- | --- |
| Lumerol K 28 | Disodium Laureth Sulfosuccinate. Co-camidopropyl Betaine. Magnesium Lauryl Sulfate | 33.0 |
| Amphotensid B4 | Cocamidopropyl Betaine | 10.0 |
| Perlglanzmittel GM 4055 | MIPA-Pareth-25 Sulfate. Glycol Stearate | 4.0 |
| Sodium Chloride | Sodium Chloride | 2.0 |
| Avocado oil | *Persea Gratissima* (Avocado) Oil | 3.0 |
| Water | Water | Ad 100 |
| Perfume oil P1. P2. P3 or P4 | Fragrance | 0.5 |
| Euxyl ® K727 | Phenoxyethanol. Methyldibromo Glutaronitrile. Isothiazolinones | 0.3 |
| Substance of formula (I) | Hydroxyacetophenone | 0.6 |

TABLE V

Cosmetic lotion for body wash with Triclosan (Amounts in % b.w.)

| Ingredients | INCI Name | Amount |
| --- | --- | --- |
| Texapon N 25 | Sodium Laureth Sulfate | 37.5 |
| Lamepon S | Potassium Cocoyl Hydrolyzed Collagen | 28.0 |
| Lamesoft LMG | Hydrogenated Tallow Glycerides. TEA-Cocoyl Hydrolyzed Collagen | 5.0 |
| Lamesoft 156 | Glyceryl Laurate. TEA-Cocoyl Hydrolyzed Collagen | 5.0 |
| Sodium Chloride | Sodium Chloride | 1.7 |
| Irgasan DP 300 | Triclosan | 0.5 |
| Water | Water | Ad 100 |

TABLE V-continued

Cosmetic lotion for body wash with Triclosan (Amounts in % b.w.)

| Ingredients | INCI Name | Amount |
|---|---|---|
| Perfume oil P1. P2. P3 or P4 | Fragrance | 0.3 |
| Euxyl ® K703 | Phenoxyethanol. Benzoic Acid. Dehydroacetic Acid | 0.4 |
| Substance of formula (I) | Hydroxyacetophenone | 0.4 |

TABLE VI

Intimate wash (Amounts in % b.w.)

| Ingredients | INCI Name | Amount |
|---|---|---|
| Tegobetaine HS | Cocamidopropyl Betaine. Glyceryl Laurate | 15.0 |
| Tagat L 2 | PEG-20 Glyceryl Laurate | 2.0 |
| Arlacide G | Chlorhexidine Digluconate | 0.1 |
| Rewoquat B 50 | Benzalkonium Chloride | 0.1 |
| Lactic Acid. 80% | Lactic Acid | 0.1 |
| Water | Water | Ad 100 |
| Perfume oil P1. P2. P3 or P4 | Fragrance | 0.2 |
| Euxyl ® K700 | Potassium Sorbate. Benzyl Alcohol. Phenoxyethanol | 0.3 |
| Substance of formula (I) | Hydroxyacetophenone | 0.5 |

TABLE VII

Liquid soap (Amounts in % b.w.)

| Ingredient | INCI | Amount |
|---|---|---|
| Deionized water | Water | 2.0 |
| Soap bases mix | Sodium tallowates/palmitates | 95.8 |
| Titanium dioxide | Titanium dioxide | 1.0 |
| Perfume oil P1. P2. P3 or P4 | Fragrance | 1.2 |
| Preservatives | Phenoxyethanol | 0.5 |
| Substance of formula (I) | Hydroxyacetophenone | 0.5 |

TABLE VIII

Shampoo (Amounts in % b.w.)

| Ingredients | Amount |
|---|---|
| Sodium lauryl ether sulfate (e.g. Texapon NSO) | 12 |
| Cocamidopropyl betaine (e.g. Dehyton K) | 2 |
| Sodium chloride | 1.4 |
| Citric acid | 1.3 |
| Perfume oil P1. P2. P3 or P4 | 0.3 |
| Phenoxyethanol. methyl-. ethyl-. butyl- and propylparaben | 0.5 |
| Substance of formula (I) | 0.5 |
| Water | Ad 100 |

TABLE IX 2-in-1 Shampoo (Amounts in % b.w.)

| Ingredients | INCI Name | Amount |
|---|---|---|
| Deionized water | Water | Ad 100 |
| Plantacare PS 10 | Sodium Laureth Sulfate. Lauryl Glucoside | 20.0 |
| Euperlan PK 771 | Glycol Distearate. Sodium Lauryl Sulfate. Cocamide MEA. Laureth-10 | 6.0 |
| Sodium chloride | Sodium Chloride | 1.4 |
| Citric acid monohydrate crystalline | Citric acid | 0.1 |
| Perfume oil P1. P2. P3 or P4 | Fragrance | 0.5 |
| Dragocid Liquid | Phenoxyethanol, Parabens | 0.5 |
| Substance of formula (I) | Hydroxyacetophenone | 0.5 |

TABLE X

Anti-dandruff Shampoo (Amounts in % b.w.)

| Ingredients | Amount |
|---|---|
| Climbazole | 0.50 |
| Sodium Laureth Sulfate | 37.00 |
| Cocamidopropyl Betaine | 8.00 |
| PEG-6 Caprylic/Capric Glycerides | 2.50 |

TABLE X-continued

Anti-dandruff Shampoo (Amounts in % b.w.)

| Ingredients | Amount |
| --- | --- |
| Laureth-2 | 2.00 |
| Water (Aqua). Glycerol. *Thymus Vulgaris* (Thyme). Flower/Leaf Extract | 0.50 |
| *Rosmarinus Officinalis* (Rosemary) Leaf Water. Water (Aqua). Butylene Glycol. Pentylene Glycol | 0.50 |
| Bisabolol | 0.10 |
| Panthenol | 0.50 |
| Polyquaternium-10 | 0.40 |
| Perfume oil P1. P2. P3 or P4 | 0.50 |
| Phenoxyethanol. Methylparaben. Ethylparaben. Butylparaben. Propylparaben. Isobutylparaben | 0.70 |
| Substance of formula (I) | 0.30 |
| Water (Aqua) | Ad 100 |

TABLE XI

Hair conditioner with Crinipan. rinse-off (Amounts in % b.w.)

| Ingredients | INCI Name | Amount |
| --- | --- | --- |
| Lanette ® O | Cetearyl Alcohol | 4.00 |
| Dragoxat 89 | Ethylhexyl Isononanoate | 2.00 |
| Genamin ® KDM-P | Behentrimonium Chloride | 1.00 |
| SF 1550 | Phenyl Trimethicone | 0.10 |
| Neo Heliopan ® BB | Benzophenone-3 | 0.10 |
| Crinipan ® AD | Climbazole | 0.80 |
| Glycerol 99.5 P. | Glycerol | 6.00 |
| Water | Water (Aqua) | Ad 100 |
| Actipone ® Alpha Pulp | Water (Aqua). Butylene Glycol. Malic Acid. *Actinidia Chinensis* (Kiwi)Fruit Juice. Citrus. *Aurantium Dulcis* (Orange). Juice. *Citrus Paradisi* (Grapefruit) Juice. *Pyrus Malus* (Apple) Juice. Trideceth-9. *PrunusAmygdalus Dulcis* (Sweet Almond) Seed Extract | 0.50 |
| Extrapone ® Bamboo P | Propylene Glycol. Water (Aqua). Butylene Glycol. *Bambusa Vulgaris* Shoot Extract | 0.50 |
| Sodium Hydroxide 10% solution | Sodium Hydroxide | 0.40 |
| Colour I | Colour | 0.60 |
| Colour II | Colour | 0.30 |
| Perfume oil P1. P2. P3 or P4 | Fragrance | 0.40 |
| Preservative | Methylparaben | 0.20 |
| Substance of formula (I) | Hydroxyacetophenone | 0.70 |

TABLE XII

Sprayable hair conditioner with zinc pyrithione. leave-on (Amounts in % b.w.)

| Ingredients | INCI Name | Amount |
| --- | --- | --- |
| Monomuls 60-35 C | Hydrogenated Palm Glycerides | 1.70 |
| Cetiol OE | Dicaprylyl Ether | 7.20 |
| Abil 100 | Dimethicone | 3.60 |
| Dehyquart F 75 | Distearoylethyl Hydroxyethylmonium. Methosulfate. Cetearyl Alcohol | 4.00 |
| Eumulgin B1 | Ceteareth-12 | 3.50 |
| Cetiol S | Diethylhexylcyclohexane | 7.20 |
| D-Panthenol | Panthenol | 0.10 |
| Glycerol 99.5 P. | Glycerol | 1.50 |
| Water | Water (Aqua) | Ad 100 |
| Actipone ® Rosemary | Water (Aqua). Propylene. Glycol. *Rosmarinus Officinalis*. (Rosemary) Leaf Extract | 0.10 |
| Frescolat ® ML Cryst. | Menthyl Lactate | 0.50 |
| Dragosantol100 | Bisabolol | 0.10 |
| Zinc Omadine | Zinc pyrithione | 0.10 |
| Perfume oil P1. P2. P3 or P4 | Fragrance | 0.40 |
| Phenonip ® | phenoxyethanol. methylparaben. ethylparaben. butylparaben. propylparaben. isobutylparaben | 0.30 |
| Substance of formula (I) | Hydroxyacetophenone | 0.5 |

TABLE XIII

Hair conditioner with UV protection (Amounts in % b.w.)

| Ingredients | INCI Name | Amount |
|---|---|---|
| Renex PEG 6000 | PEG-150 | 2.50 |
| Hair Conditioner Base | Cetyl alcohol. behentrimonium chloride. *Triticum Vulgare* (Wheat) bran extract. linoleic acid | 3.00 |
| PCL-Solid | Stearyl heptanoate. stearyl caprylate | 0.50 |
| Dow Corning 5200 | Laurylmethicone copolyol | 0.50 |
| Natrosol 250 HR | Hydroxyethylcellulose | 0.50 |
| Benzophenone-4 | Benzophenone-4 | 1.00 |
| Neo Heliopan AP | Disodiumphenyldibenz-imidazole tetrasulphonate | 1.00 |
| Amino methyl propanol | Amino methyl propanol | 2.00 |
| Dow Corning 949 cationic emulsion | Amodimethicone. cetrimonium chloride. trideceth-12 | 2.00 |
| Perfume oil P1. P2. P3 or P4 | Fragrance | 0.80 |
| 1.2-hexanediol | 1.2-hexanediol | 0.50 |
| Substance of formula (I) | Hydroxyacetophenone | 0.50 |
| Water | Water (Aqua) | Ad 100 |

TABLE XIV

Shower gel (Amounts in % b.w.)

| Ingredients | INCI | Amount |
|---|---|---|
| Deionized water | Water | Ad 100 |
| Plantacare PS 10 | Sodium Laureth Sulfate. Lauryl Glucoside | 20.0 |
| Sodium chloride | Sodium Chloride | 1.4 |
| Citric acid monohydrate crystalline | Citric Acid | 1.3 |
| Perfume oil P1. P2. P3 or P4 | Fragrance | 0.6 |
| SymDiol ®68 | 1.2-hexanediol. caprylyl glycol | 0.4 |
| Substance of formula (I) | Hydroxyacetophenone | 0.4 |

TABLE XV

Shaving foam (Amounts in % b.w.)

| Ingredients | Amount |
|---|---|
| Dem. Water | 77.2 |
| Triethanolamine | 4.0 |
| Edenor L2 SM (Stearinic acid. Palmitinic acid) (Cognis) | 5.3 |
| Laureth-23 | 3.0 |
| Stearylalcohol | 0.5 |
| Sodium lauryl sulfate | 3.0 |
| Extrapone Seaweed (water. propylene glycol. potassium iodide. *Fucus Vesiculosus* Extract) | 1.0 |
| Dragosantol (Bisabolol. Farnesol) | 0.1 |
| Perfume oil P1. P2. P3 or P4 | 1.0 |
| euxyl ® K220 (Methylisothiazolinone. Ethylhexylglyerol) | 0.6 |
| Substance of formula (I) | 0.3 |
| Propane. butane 4.2 Bar | 4.0 |

TABLE XVI

Depilatory cream (Amounts in % b.w.)

| Ingredients | Amount |
|---|---|
| Cetearyl alcohol | 10.0 |
| Ceteareth-12 | 2.0 |
| PCL-Liquid (Cetearylethylhexanoate. Isopropylmyristate) | 3.0 |
| Dragosantol (Bisabolol. Farnesol) | 0.1 |
| Edenor L2 SM (Stearinic acid. Palmitinic acid) | 1.0 |
| Dem. Water | 52.2 |
| Urea | 5.0 |
| Dem. Water | 10.0 |
| Calcium thioglycolate | 6.0 |
| Sodium hydroxide solution. 10% | 10.0 |
| Perfume oil P1. P2. P3 or P4 | 0.5 |
| Neo Dragocid Powder (Methyl parabene. sorbinic acid. Dehydro acetic acid. Propyl parabene) | 0.2 |
| Substance of formula (I) | 0.4 |

TABLE XVII

After Shave Tonic (Amounts in % b.w.)

| Ingredients | INCI | Amount |
|---|---|---|
| SymSol ® PF-3 | Water (Aqua). Pentylene Glycol. Sodium Lauryl Sulfoacetate. SodiumOleoyl Sarcosinate. Sodium Chloride. Disodium Sulfoacetate. SodiumOleate. Sodium Sulfate | 3.00 |
| SymSitive ® 1609 | Pentylene Glycol. 4-t-Butylcyclohexan ol | 1.00 |
| Frescolat ® ML | Menthyl Lactate | 0.30 |
| Glycerol 99.5 P. | Glycerol | 5.00 |
| Water | Water (Aqua) | Ad 100 |
| Extrapone ® Glacier Water GW | Glycerol. Water (Aqua) | 1.00 |
| SymCalmin ® | Butylene Glycol. Pentylene Glycol. Hydroxyphenyl Propamidobenzoic Acid | 0.50 |
| Dragosine ® | Carnosine | 0.10 |
| Hydrolite ® 5 | Pentylene Glycol | 5.00 |
| Ethanol 96% | Alcohol Denat. | 5.00 |
| Colour Pigment | Colour Pigment | 0.05 |
| Perfume oil P1. P2. P3 or P4 | Parfum | 0.15 |
| Substance of formula (I) | Hydroxyacetophenone | 1.00 |

TABLE XVIII

Deodorant formulation in the form of a roll-on gel (Amounts in % b.w.)

| Ingredients | Amount |
|---|---|
| 1.3-butylene glycol | 2.00 |
| PEG-40-hydrogenated castor oil | 2.00 |
| Hydroxyethylcellulose | 0.50 |
| Perfume oil P1. P2. P3 or P4 | 0.30 |
| 1.3-propanediol | 0.50 |
| 3-phenylpropanol | 0.40 |
| Ethylhexyl glycerin | 0.10 |
| Substance of formula (I) | 0.50 |
| Water | ad 100.00 |

TABLE XIX

Clear deo anti-perspirant roll-on (Amounts in % b.w.)

| Ingredients | INCI | Amount |
|---|---|---|
| Methocel E4M Premium | Hydroxypropyl Methylcellulose | 0.50 |
| Water | Water (Aqua) | Ad 100 |
| Neo-PCL Water Soluble N | Trideceth-9. PEG-5 Ethylhexanoate. Water (Aqua) | 1.00 |
| Solubilizer | PEG-40 Hydrogenated Castor Oil. Trideceth-9. Propylene Glycol. Water (Aqua) | 3.00 |
| Deolite | Dimethyl Phenylpropanol. Pentylene Glycol | 0.50 |
| Locron LW | Aluminium Chlorohydrate | 25.00 |
| Aloe Vera Gel Concentrate 10/1 | *Aloe Barbadensis* Leaf Juice | 1.00 |
| Propylene Glycol -1.2 99 P GC | Propylene Glycol | 4.00 |
| Ethanol 96% | Alcohol Denat. | 30.00 |
| Perfume oil P1. P2. P3 or P4 | Parfum | 1.00 |
| Substance of formula (I) | Hydroxyacetophenone | 0.25 |

TABLE XX

Deodorant stick (Amounts in % b.w.)

| Ingredients | Amount |
| --- | --- |
| Sodium stearate | 8.00 |
| PPG-3 Myristyl ether | 70.00 |
| 1.2-propylene glycol | 10.00 |
| 1,1-dimethyl-3-phenylpropanol | 0.20 |
| 2-butyloctanoic acid | 0.20 |
| Perfume oil P1, P2, P3 or P4 | 0.60 |
| Heptoxy-1.2-propanediol | 0.20 |
| Phenoxyethanol | 0.30 |
| Substance of formula (I) | 0.50 |
| Water | Ad 100 |

TABLE XXI

Zirconium suspensoid antiperspirant stick (Amounts in % b.w.)

| Ingredients | INCI | Amount |
| --- | --- | --- |
| PCL Liquid 100 | Cetearyl ethylhexanonate | to 100 |
| Silicone Fluid 345 | Cyclomethicone | 10.00 |
| CRODACOL C90 | Cetyl Alcohol | 8.00 |
| SYNCROWAX HGLC | C18-36 Triglyceride | 8.00 |
| CRODAMOL PTC | Pentaerythritol Tetracaprylate/Caprate | 5.00 |
| SYNCROWAX HRC | Tribehenin | 4.00 |
| VOLPO N5 | Oleth-5 | 1.00 |
| Titanium Dioxide | | 1.00 |
| Rezal 36GP | Aluminium Tetrachlorohydrex GLY | 20.00 |
| Dry Flo C | Aluminium Starch Octenyl Succinate | 22.50 |
| Perfume oil P1, P2, P3 or P4 | Parfum | 0.60 |
| Preservative | Phenoxyethanol | 0.40 |
| Hexoxy-1.2-propanediol | | 0.10 |
| Substance of formula (I) | Hydroxyacetophenone | 0.40 |

TABLE XXII

Deodorant pump spray with SymClariol (Amounts in % b.w.)

| Ingredients | INCI | Amount |
| --- | --- | --- |
| SymClariol ® | Decylene Glycol | 0.50 |
| Solubilizer | PEG-40 Hydrogenated Castor Oil, Trideceth-9, Propylene Glycol, Water (Aqua) | 4.00 |
| Neo-PCL Water Soluble N | Trideceth-9, PEG-5 Ethylhexanoate, Aqua | 1.50 |
| SymRelief ® | Bisabolol, *Zingiber Officinale* (Ginger) Root Extract | 0.10 |
| Water | Water (Aqua) | Ad 100 |
| 1.2 Propylene Glycol | Propylene Glycol | 6.00 |
| Perfume oil P1, P2, P3 or P4 | Perfume | 0.40 |
| SymDiol ® 68 | 1,2-Hexanediol, Caprylyl Glycol | 0.20 |
| 4-hydroxyacetophenone | Hydroxyacetophenone | 0.40 |

TABLE XXIII

Antiperspirant formulations (Amounts in % b.w.)

| Ingredients | Amounts |
| --- | --- |
| Reach AZP-908 SUF | 24.00 |
| Cyclomethicone (Pentamer) | Ad 100 |
| Polydecene (Silkflo 364 NF) | 17.50 |
| Neo Heliopan OS (ethylhexyl salicylate) | 2.50 |
| L-Menthyl lactate (Frescolate ML) | 0.25 |
| Polyethylene | 3.00 |
| Hydrogenated castor oil | 2.00 |
| Promyristyl PM-3 | 7.00 |
| PEG-8 Distearate | 3.00 |
| Silicon dioxide (Cab-O-Sil M-5) | 1.00 |
| Stearyl alcohol | 15.00 |
| Octyldodecanol | 0.10 |
| Perfume oil P1, P2, P3 or P4 | 0.80 |
| 3-Phenylpropanol | 0.40 |
| Substance of formula (I) | 0.60 |

TABLE XXIV

Deodorant spray with Triclosan (Amounts in % b.w.)

| Ingredients | Amount |
| --- | --- |
| PEG-40-hydrogenated castor oil | 3.00 |
| Ethylhexylglycerol (Octoxyglycerol) | 0.80 |
| Ethanol | 40.00 |
| Citrate buffer | 0.50 |
| 1.2-Hexanediol/1.2-octanediol (1:1) | — |
| Triclosan ® (5-chloro-2-(2,4-dichlorophenoxy)phenol) | 0.25 |
| 2-Benzylheptan-1-ol (Jasmol) | — |
| Perfume oil P1, P2, P3 or P4 | 0.75 |
| Phenoxyethanol | 0.40 |

TABLE XXIV-continued

Deodorant spray with Triclosan (Amounts in % b.w.)

| Ingredients | Amount |
| --- | --- |
| Substance of formula (I) | 0.40 |
| Water | Ad 100 |

TABLE XXV

O/W lotion (Amounts in % b.w.)

| Ingredients | Amount |
| --- | --- |
| Paraffin oil | 5.00 |
| Isopropyl palmitate | 5.00 |
| Cetyl alcohol | 2.00 |
| Beeswax | 2.00 |
| Ceteareth-20 | 2.00 |
| PEG-20-glyceryl stearate | 1.50 |
| Glycerol | 3.00 |
| Perfume oil P1. P2. P3 or P4 | 0.30 |
| Methylparaben | 0.30 |
| Substance of formula (I) | 0.60 |
| Water | ad 100.00 |

TABLE XXVI

Body lotion (Amounts in % b.w.)

| Ingredients | Amount |
| --- | --- |
| Cetearyl Alcohol | 2.00 |
| Ethylhexyl Isononanoate | 5.00 |
| Cetearyl Ethylhexanoate. Isopropyl Myristate | 3.00 |
| Glyceryl Oleate Citrate. Caprylic/Capric Triglyceride | 4.00 |
| Water (Aqua) | 79.50 |
| Carbomer | 0.30 |
| Sodium Benzoate | 0.100 |
| Propylene Glycol | 5.00 |
| Sodium Hydroxide 30% solution | 0.30 |
| Perfume oil P1. P2. P3 or P4 | 0.30 |
| Triethylene Glycol. Imidazolidinyl Urea. Methylparaben. Propylparaben. Dehydroacetic Acid | 0.30 |
| Substance of formula (I) | 0.20 |

TABLE XXVII

Cream (Amounts in % b.w.)

| Ingredients | Amount |
| --- | --- |
| Paraffin oil | 10.00 |
| Ozokerite | 4.00 |
| Vaseline | 4.00 |
| Vegetable oil | 10.00 |
| Wool wax alcohol | 2.00 |
| Aluminium stearate | 0.40 |
| Perfume oil P1. P2. P3 or P4 | 0.70 |
| 1.2-pentanediol | 2.00 |
| Phenoxyethanol | 0.50 |
| Substance of formula (I) | 0.50 |
| Water | ad 100.00 |

TABLE XXVIII

Cream (Amounts in % b.w.)

| Ingredients | INCI | Amount |
| --- | --- | --- |
| Dracorin ® CE | Glyceryl Stearate Citrate | 1.00 |
| Lanette ® O | Cetearyl Alcohol | 2.00 |
| Cutina ® GMS-V | Glyceryl Stearate | 1.00 |
| Tegosoft ® MM | Myristyl Myristate | 1.00 |
| Xiameter ® PMX-0246. Cyclosiloxane | Cyclohexasiloxane (and) Cyclopentasiloxane | 0.50 |
| Dragoxat ® 89 | Ethylhexyl Isononanoate | 2.00 |
| PCL-Liquid 100 | Cetearyl Ethylhexanoate | 4.00 |
| Neutral Oil | Caprylic/Capric Triglyceride | 4.00 |
| Carbopol ® Ultrez 21 | Acrylates/C10-30 Alkyl Acrylate Crosspolymer | 0.20 |
| Keltrol ® CG-T | Xanthan Gum | 0.10 |
| Water | Water (Aqua) | Ad 100 |
| Glycerol 99.5 P. | Glycerol | 3.00 |
| Propylene Glycol-1.2 99 P GC | Propylene Glycol | 2.00 |
| Sodium Benzoate | Sodium Benzoate | 0.10 |
| Sodium Hydroxide 10% solution | Sodium Hydroxide | 0.50 |
| Perfume oil P1. P2. P3 or P4 | Perfume | 0.30 |
| Euxyl ® K702 | Dehydroacetic Acid. Benzoic Acid. Phenoxyethanol.Polyaminopropyl Biguanide. Ethylhexylglycerin | 0.30 |
| 4-hydroxyacetophenone | Hydroxyacetophenone | 0.70 |

TABLE XXIX

Hand and body cream (Amounts in % b.w.)

| Ingredients | INCI | Amount |
| --- | --- | --- |
| Dracorin ® GOC | Glyceryl Oleate Citrate. Caprylic/Capric Triglyceride | 2.00 |
| PCL-Solid | Stearyl Heptanoate. Stearyl Caprylate | 2.50 |
| Lanette ® O | Cetearyl Alcohol | 1.50 |
| Cutina ® GMS-V | Glyceryl Stearate | 1.00 |
| Dragoxat ® 89 | Ethylhexyl Isononanoate | 3.00 |
| PCL-Liquid 100 | Cetearyl Ethylhexanoate | 7.00 |
| Isodragol ® | Triisononanoin | 4.00 |
| Xiameter ® PMX-0345 Cyclosiloxane | Cyclopentasiloxane (and) Cyclohexasiloxane | 0.50 |
| Water | Water (Aqua) | Ad 100 |
| Carbopol ® Ultrez 21 | Acrylates/C10-30 Alkyl Acrylate Crosspolymer | 0.20 |
| Keltrol ® CG-RD | Xanthan Gum | 0.10 |
| Glycerol 85 P. | Glycerol | 3.00 |
| DragoBetaGlucan | Water (Aqua). Butylene Glycol. Glycerol. *Avena Sativa* (Oat) Kernel Extract | 1.50 |
| Potassium Sorbat | Potassium Sorbate | 0.10 |
| Sodium Hydroxide 10% solution | Sodium Hydroxide | 0.50 |
| Perfume oil P1. P2. P3 or P4 | Parfum | 0.20 |
| Euxyl ® K300 | Methyl-. Butyl-. Ethyl-. Propyl. Isobutylparaben. Phenoxyethanol. | 0.30 |
| 4-hydroxyacetophenone | Hydroxyacetophenone | 0.30 |

TABLE XXX

Face cream (Amounts in % b.w.)

| Ingredients | INCI | Amount |
| --- | --- | --- |
| Emulsiphos ® | Potassium Cetyl Phosphate. Hydrogenated Palm Glycerides | 1.50 |
| Cutina ® GMS-V | Glyceryl Stearate | 1.70 |
| Lanette ® O | Cetearyl Alcohol | 3.00 |
| Tegosoft ® MM | Myristyl Myristate | 1.00 |
| PCL-Liquid 100 | Cetearyl Ethylhexanoate | 1.00 |
| Isodragol ® | Triisononanoin | 3.00 |
| Dragoxat ® 89 | Ethylhexyl Isononanoate | 4.00 |
| Avocado Oil | *Persea Gratissima* (Avocado) Oil | 3.00 |
| Abil ® 350 | Dimethicone | 0.50 |
| Covi-ox ® T-70 | Tocopherol | 0.10 |
| Edeta ® BD | Disodium EDTA | 0.10 |
| Carbopol ® Ultrez 21 | Acrylates/C10-30 Alkyl Acrylate Crosspolymer | 0.30 |
| Keltrol ® CG-RD | Xanthan Gum | 0.150 |
| Water | Water (Aqua) | Ad 100 |
| Glycerol 99.5 P. | Glycerol | 4.00 |
| Propylene Glycol-1.2 99 P GC | Propylene Glycol | 3.00 |
| SymMatrix ® | Maltodextrin. *Rubus Fruticosus* (Blackberry) Leaf Extract | 0.50 |
| Sodium Hydroxide 10% solution | Sodium Hydroxide | 0.50 |
| Perfume oil P1. P2. P3 or P4 | Parfum | 0.30 |
| Euxyl ® K712 | Sodium Benzoate. Potassium Sorbate | 0.20 |
| 4-hydroxyacetophenone | Hydroxyacetophenone | 0.60 |

TABLE XXXI

Moisturizing body care cream (Amounts in % b.w.)

| Ingredient | Amount |
| --- | --- |
| PEG-7 hydrogenated castor oil | 6.00 |
| Cetearyl ethyl hexanoate | 10.00 |
| Isopropyl myristate | 5.00 |
| Mineral oil | 7.00 |
| Shea Butter (*Butyrospermum parkii*) | 0.50 |
| Aluminum stearate | 0.50 |
| Magnesium stearate | 0.50 |
| Bisabolol | 0.20 |
| Quaternium-18-Hectorit | 0.70 |
| Dipropylene glycol | 5.0 |
| Magnesium sulfate | 0.70 |
| Pentylene glycol | 4.00 |
| Perfume oil P1. P2. P3 or P4 | 0.30 |
| Preservative (Phenoxyethanol) | 0.20 |
| Substance of formula (I) | 0.40 |
| Aqua dem. | 58.90 |

TABLE XXXII

Anti-wrinkle cream (Amounts in % b.w.)

| Ingredients | Amount |
| --- | --- |
| Glyceryl Stearate Citrate | 1.00 |
| Glyceryl Laurate | 1.00 |
| Cetearyl Alcohol (and) Myristyl Myristate | 3.00 |
| Cetearyl Ethylhexanoate | 4.00 |
| Mineral oil | 4.00 |
| Cyclopentasiloxane. Cyclohexasiloxane | 0.50 |
| Acrylates/C10-30 Alkyl Acrylate Crosspolymer | 0.20 |
| Water | Ad 100 |
| 1.2-Hexanediol | 2.00 |
| Sodium Hydroxide 10% solution | 0.10 |
| *Narcissus Tazetta* Bulb Extract | 1.00 |
| Perfume oil P1. P2. P3 or P4 | 0.30 |
| Preservative (Phenoxyethanol) | 0.50 |
| Substance of formula (I) | 0.50 |

TABLE XXXIII

Functional skin oil for disinfection (Amounts in % b.w.)

| Ingredients | INCI | Amount |
| --- | --- | --- |
| Neutral Oil | Caprylic/Capric Triglyceride | Ad 100 |
| Sweet Almond Oil | *Prunus Dulcis* | 20.00 |
| Dragoxat ® 89 | Ethylhexyl Isononanoate | 4.00 |
| Isopropyl Palmitate | Isopropyl Palmitate | 6.00 |
| PCL-Liquid 100 | Cetearyl Ethylhexanoate | 15.00 |
| Dragosantol ® 100 | Bisabolol | 0.20 |
| Retinyl Acetate In Oil (1 Mio. Ie/G) | Retinyl Acetate | 0.50 |
| Vitamin E Acetate | Tocopheryl Acetate | 0.50 |
| Covi-ox ® T-70 | Tocopherol | 0.10 |
| Perfume oil P1. P2. P3 or P4 | Parfum | 0.30 |
| Preservative | Methyl-. Butyl-. Ethyl-. Propylparaben | 0.30 |
| 4-hydroxyacetophenone | Hydroxyacetophenone | 0.40 |

TABLE XXXIV

Septic wound cream (Amounts in % b.w.)

| Ingredients (INCI) | Amount |
| --- | --- |
| Sorbitan Isostearate. Hydrogenated Castor Oil. Ceresin. Beeswax (Cera Alba) | 6.00 |
| Petrolatum | 21.00 |
| Cera Alba | 5.00 |
| Cetearyl Alcohol | 7.00 |
| *Prunus Dulcis* | 7.00 |
| Lanolin | 5.00 |
| Paraffinum Liquidum | 12.00 |
| Perfume oil P1. P2. P3 or P4 | 0.30 |
| Water (Aqua) | Ad 100 |
| Panthenol | 7.00 |
| Magnesium Sulfate | 0.70 |
| Pentylene Glycol | 1.00 |
| Tocopheryl Acetate | 1.00 |
| Octenidine dihydrochloride | 0.10 |
| Phenoxyethanol | 0.50 |
| Substance of formula (I) | 0.50 |

TABLE XXXV

Moisturizing and disinfecting face mask (Amounts in % b.w.)

| Ingredients | INCI | Amount |
| --- | --- | --- |
| Water | Water (Aqua) | Ad 100 |
| Stabileze QM | PVM/Ma Decadiene Crosspolymer | 0.50 |
| Biotive ® L-Arginine | Arginine | 0.75 |
| Actipone ® *Laminaria Saccharina* GW | Glycerol. Water (Aqua). *Laminaria Saccharina* Extract | 1.00 |
| Extrapone ® Cucumber | Water (Aqua). Propylene Glycol. *Cucumis Sativus* (Cucumber) Juice | 1.00 |
| Glycerol 99.5 P. | Glycerol | 7.00 |
| Neo Actipone ® Soap Nutshell | *Sapindus Mukurossi* Peel Extract | 0.50 |
| Colour I | Colour | 0.01 |
| Hydrolite ® 5 | Pentylene Glycol | 5.00 |
| Solubilizer | PEG-40 Hydrogenated Castor Oil. Trideceth-9. Water (Aqua) | 0.60 |
| Perfume oil P1. P2. P3 or P4 | Parfum | 0.08 |
| Preservative | Phenoxyethanol | 0.40 |
| 4-hydroxyacetophenone | Hydroxyacetophenone | 0.40 |

TABLE XXXVI

Sprayable disinfecting gel (Amounts in % b.w.)

| Ingredients | INCI | Amount |
| --- | --- | --- |
| Water | Water (Aqua) | Ad 100 |
| Stabileze QM | PVM/Ma Decadiene Crosspolymer | 0.25 |
| Sodium Hydroxide 10% solution | Sodium Hydroxide | 0.40 |
| Coffein pure | Caffeine | 0.50 |
| Extrapone ® Horse Chestnut | Propylene Glycol. Water (Aqua). Glucose. *Aesculus Hippocastanum* (Horse Chestnut) Seed Extract. Lactic Acid | 1.00 |

TABLE XXXVI-continued

Sprayable disinfecting gel (Amounts in % b.w.)

| Ingredients | INCI | Amount |
|---|---|---|
| Hydrolite ® 5 | Pentylene Glycol | 3.00 |
| 1.3 Butylene Glycol | Butylene Glycol | 5.00 |
| Biotive ® Esculin Sesquihydrate | Esculin | 0.30 |
| Ethanol 96% | Alcohol Denat. | 10.00 |
| Solubilizer | PEG-40 Hydrogenated Castor Oil. Trideceth-9. Water (Aqua) | 0.50 |
| Perfume oil P1. P2. P3 or P4 | Parfum | 0.20 |
| Octenidine dihydrochloride | | 0.10 |
| Preservative | Phenoxyethanol | 0.70 |
| 4-hydroxyacetophenone | Hydroxyacetophenone | 0.30 |

TABLE XXXVII

Mineral wash and cleaning gel (Amounts in % b.w.)

| Ingredients | INCI | Amount |
|---|---|---|
| Water | Water (Aqua) | Ad 100 |
| Pionier ® NP 37 G | Sodium Carbomer | 1.50 |
| SymSol ® PF-3 | Water (Aqua). Pentylene Glycol. Sodium Lauryl Sulfoacetate. SodiumOleoyl Sarcosinate. Sodium Chloride. Disodium Sulfoacetate. Sodium Oleate. Sodium Sulfate | 5.00 |
| Hydroviton ® 24 | Water (Aqua). Pentylene Glycol. Glycerol. Sodium Lactate. Lactic Acid. Serine. Urea. Sorbitol. Sodium Chloride. Allantoin | 1.00 |
| Extrapone ® Silk GW | Water (Aqua). Glycerol. Hydrolyzed Silk | 1.00 |
| Hydrolite ® 5 | Pentylene Glycol | 4.00 |
| Actipearls Red Star # DH10402/6 | Water (Aqua). Propylene Glycol. Algin. Gellan Gum. Xanthan Gum. Calcium Chloride. CI 12490 (Pigment Red 5). Mica (CI 77019). Titanium Dioxide (CI 77891) | 1.00 |
| Perfume oil P1. P2. P3 or P4 | Parfum | 0.50 |
| 3-Phenylpropanol | | 0.70 |
| 4-hydroxyacetophenone | Hydroxyacetophenone | 0.30 |

TABLE XXXVIII

Anti-acne wash (Amounts in % b.w.)

| Ingredients (INCI) | Amount |
|---|---|
| Water (Aqua) | 45.70 |
| Polyquaternium-7 | 0.50 |
| Cocamidopropyl Betaine 9.000 | 9.00 |
| Coco Glucoside 2.000 | 2.00 |
| Polysorbate 80. Glycerol. *Gossypium Herbaceum*. (Cotton) Seed Oil. Water (Aqua) | 1.00 |
| Trideceth-9. PEG-5 Ethylhexanoate. Water (Aqua) | 1.00 |
| Glycereth-90 Isostearate. Laureth-2 | 0.50 |
| Sodium Laureth Sulfate 37.000 | 37.00 |
| Glycerol. *Triticum Vulgare* (Wheat) Gluten. Water (Aqua) | 1.00 |
| Sodium Chloride | 0.30 |
| Perfume oil P1. P2. P3 or P4 | 1.00 |
| Phenoxyethanol. Methylparaben. Ethylparaben. Butylparaben. Propylparaben. Isobutylparaben | 0.30 |
| Substance of formula (I) | 0.50 |

TABLE XXXIX

Cosmetic sun protection composition (Amounts in % b.w.)

| Ingredient | Amount |
|---|---|
| Ethylhexyl cinnamic acid | 7.50 |
| Benzophenon-3 | 2.00 |
| Polyglyceryl dimer soyate | 0.80 |
| Sorbitane stearate | 1.00 |
| Tocopheryl acetate | 0.50 |
| Glyceryl stearate. PEG-100 Stearate | 3.00 |
| PEG-40. hydrogenated castor oil | 1.00 |
| Titanium dioxide. aluminum oxide hydrate. Dimethicon/Methicon Copolymer | 3.00 |
| *Butyrospermum parkii* (Shea Butter) | 1.00 |
| $C_{12-15}$ alkyl benzoate | 6.50 |
| Butylene glycol | 5.00 |
| Xanthan gum | 0.30 |
| Disodium EDTA | 0.10 |
| Allantoin | 0.10 |
| Polyacryl amide. $C_{13-14}$ isoparaffin. Laureth-7 | 1.00 |
| Pentylene glycol | 5.00 |
| 4-t Butylcyclohexanol | 1.00 |
| Perfume oil P1. P2. P3 or P4 | 0.30 |
| Preservatives (Methyl-. Butyl-. Ethyl-. Propylparaben. Phenoxyethanol) | 0.30 |
| Substance of formula (I) | 0.60 |
| Aqua dem. | Ad 100 |

TABLE XXXX

Sun protection spray (Amounts in % b.w.)

| Ingredients | INCI | Amount |
|---|---|---|
| Water. demineralized | Water (aqua) | 69.50 |
| Glycerol | Glycerol | 4.00 |
| 1.3 butylene glycol | Butylene glycol | 5.00 |
| D-Panthenol | Panthenol | 0.50 |
| Lara Care A-200 | Galactoarabinan | 0.25 |
| Baysilone oil M 10 | Dimethicone | 1.00 |
| Edeta BD | Disodium EDTA | 0.10 |
| Copherol 1250 | Tocopheryl acetate | 0.50 |
| Cetiol OE | Dicaprylyl ether | 3.00 |
| Neo Heliopan ® HMS | Homosalate | 5.00 |
| Neo Heliopan ® AV | Ethylhexyl methoxycinnamate | 6.00 |
| Neo Heliopan ® 357 | Butyl methoxydibenzoylmethane | 1.00 |
| Corapan TQ | Diethylhexylnaphthalate | 2.00 |
| Alpha Bisabolol | Bisabolol | 0.10 |
| Pemulen TR-2 | Acrylates/C10-30 alkyl acrylate crosspolymer | 0.25 |
| NaOH. 10% | Sodium hydroxide | 0.60 |
| Perfume oil P1. P2. P3 or P4 | Fragrance | 0.20 |
| Phenoxyethanol | Phenoxyethanol | 0.40 |
| Solbrol M | Methylparaben | 0.10 |
| Solbrol P | Propylparaben | 0.10 |
| 4-hydroxyacetophenone | Hydroxyacetophenone | 0.50 |

TABLE XXXXI

Sunscreen spray O/W. SPE 15-20 (Amounts in % b.w.)

| Ingredients | INCI | Amount |
|---|---|---|
| Dracorin ® GOC | Glyceryl Oleate Citrate. Caprylic/Capric Triglyceride | 2.00 |
| Corapan ® TQ | Diethylhexyl 2.6-Naphthalate | 3.00 |
| Neo Heliopan ® HMS | Homosalate | 7.00 |
| Neo Heliopan ® OS | Ethylhexyl Salicylate | 5.00 |
| Neo Heliopan ® 357 | Butyl Methoxydibenzoylmethane | 3.00 |
| Isoadipate | Diisopropyl Adipate | 6.00 |
| Baysilone ® Oil M10 | Dimethicone | 1.00 |
| Edeta ® BD | Disodium EDTA | 0.10 |
| Vitamin E Acetate | Tocopheryl Acetate | 0.50 |
| Dragosantol ® 100 | Bisabolol | 0.10 |
| Pemulen ® TR-2 | Acrylates/C10-30 Alkyl Acrylate Crosspolymer | 0.25 |
| Water | Water (Aqua) | Ad 100 |
| Glycerol 99.5 P. | Glycerol | 4.00 |
| Butylene Glycol | Butylene Glycol | 5.00 |
| Neo Heliopan ® Hydro (103089). used as 25% aq. solution neutralized with Biotive ® L-Arginine | Phenylbenzimidazole Sulfonic Acid | 8.00 |
| Biotive ® L-Arginine | Arginine | 0.55 |
| Perfume oil P1. P2. P3 or P4 | Fragrance | 0.40 |
| Sobrol M | Methylparaben | 0.30 |
| 4-hydroxyacetophenone | Hydroxyacetophenone | 0.60 |

TABLE XXXXII

Sun protection soft cream (W/O). SPF 40 (Amounts in % b.w.)

| Ingredients | INCI | Amount |
|---|---|---|
| Dehymuls PGPH | Polyglyceryl-2 dipolyhydroxystearate | 5.00 |
| Copherol 1250 | Tocopheryl acetate | 0.50 |
| Permulgin 3220 | Ozocerite | 0.50 |
| Zinc stearate | Zinc stearate | 0.50 |
| Tegosoft TN | C12-15 Alkyl benzoate | 10.00 |
| Neo Heliopan ® E1000 | Isoamyl-p-methoxycinnamate | 2.00 |
| Neo Heliopan ® 303 | Octocrylene | 5.00 |
| Neo Heliopan ® MBC | 4-Methylbenzylidene camphor | 3.00 |
| Zinc oxide. neutral | Zinc oxide | 5.00 |
| Water. distilled | Water (aqua) | Add 100 |
| EDETA BD | Disodium EDTA | 0.10 |
| Glycerol | Glycerol | 4.00 |
| Magnesium sulfate | Magnesium sulfate | 0.50 |
| Perfume oil P1. P2. P3 or P4 | Parfum | 0.30 |
| Symdiol ® 68 | 1.2-Hexanediol. Caprylylglycol | 0.30 |
| Substance of formula (I) | | 0.80 |

TABLE XXXXIII

Sun protection milk (W/O) (Amounts in % b.w.)

| Ingredients | INCI | Amount |
|---|---|---|
| Dehymuls PGPH | Polyglyceryl-2 dipolyhydroxystearate | 3.00 |
| Beeswax 8100 | Beeswax | 1.00 |
| Monomuls 90-0-18 | Glyceryl oleate | 1.00 |
| Zinc stearate | Zinc stearate | 1.00 |
| Cetiol SN | Cetearyl isononanoate | 5.00 |
| Cetiol OE | Dicaprylyl ether | 5.00 |
| Tegosoft TN | C12-15 alkyl benzoate | 4.00 |
| Vitamin E | Tocopherol | 0.50 |
| Neo Heliopan ® OS | Ethylhexyl salicylate | 5.00 |
| Neo Heliopan ® AV | Ethylhexyl methoxycinnamate | 7.50 |
| Uvinul ® T150 | Ethylhexyl triazone | 1.50 |
| Water. distilled | Water (Aqua) | To 100 |
| Trilon BD | Disodium EDTA | 0.10 |
| Glycerol | Glycerol | 5.00 |
| Neo Heliopan ® AP 10% solution. neutralized with NaOH | Disodium phenyl dibenzimidazole tetrasulfonate | 15.00 |
| Perfume oil P1. P2. P3 or P4 | Parfum | 0.25 |
| Alpha bisabolol | Bisabolol | 0.10 |
| SymOcide ® PT | Phenoxyethanol. Tropolone | 0.25 |
| 4-hydroxyacetophenone | Hydroxyacetophenone | 0.25 |

TABLE XXXXIV

After sun gel (Amounts in % b.w.)

| Ingredients | INCI | Amount |
|---|---|---|
| SymSol ® PF-3 | Water (Aqua). Pentylene Glycol. Sodium Lauryl Sulfoacetate. SodiumOleoyl Sarcosinate. Sodium Chloride. Disodium Sulfoacetate. Sodium Oleate. Sodium Sulfate | 3.000 |
| Glycerol 99.5 P. | Glycerol | 5.000 |
| SymHelios ® 1031 | Benzylidene Dimethoxydimethylin danone | 0.100 |
| Water | Water (Aqua) | Ad 100 |
| Pemulen ® TR-2 | Acrylates/C10-30 Alkyl Acrylate Crosspolymer | 1.000 |
| D-Panthenol 75 W | Panthenol | 0.500 |
| SymFinity ® 1298 | *Echinacea Purpurea* Extract | 0.100 |
| Extrapone ® Pearl GW | Water (Aqua). Glycerol. Hydrolyzed Pearl. Xanthan Gum | 1.000 |
| Sodium Hydroxide 10% solution | Sodium Hydroxide | 2.500 |
| Ethanol 96% | Alcohol Denat. | 15.000 |
| Perfume oil P1. P2. P3 or P4 | Parfum | 0.20 |
| SymOcide ® PS | Phenoxyethanol. 1.2-Hexanediol. Decyleneglycol | 0.50 |
| 4-hydroxyacetophenone | Hydroxyacetophenone | 0.50 |

TABLE XXXXV

After sun lotion (Amounts in % b.w.)

| Ingredients | Amount |
|---|---|
| Acrylate/C10-30 alkylacrylate crosspolymer | 0.4 |
| Cetearylethyl hexanoate | 15.0 |
| Bisabolol | 0.2 |
| Tocopheryl acetate | 1.0 |
| Panthenol | 1.0 |
| Alcohol | 15.0 |
| Glycerol | 3.0 |
| Perfume oil P1. P2. P3 or P4 | 0.30 |
| 1.2-Hexanediol | 0.60 |
| Substance of formula (I) | 0.30 |
| Pentylene glycol | 4.0 |
| Aqua dem. | Ad 100 |
| Triethanolamine | 0.2 |

TABLE XXXXVI

Hair styling gel (Amounts in % b.w.)

| Ingredients | Amount |
|---|---|
| Water | Ad 100 |
| PVM/MA Decadiene Crosspolymer | 0.60 |
| PVP | 3.00 |
| Isocetyl Stearate | 4.00 |
| Ethylhexyl Methoxycinnamate | 0.50 |
| Aminomethyl Propanol | 0.40 |
| Perfume oil P1. P2. P3 or P4 | 0.60 |
| SymDiol ® 68T (1.2-Hexanediol. 1.2-Octanediol. Tropolone) | 0.30 |
| Phenoxyethanol | 0.20 |
| Substance of formula (I) | 0.40 |

TABLE XXXXVII

Silicone emulsion (Amounts in % b.w.)

| Ingredients | Amount |
|---|---|
| Potassium Cetyl Phosphate. Hydrogenated Palm Glycerides | 1.00 |
| Cyclohexasiloxane | 4.00 |
| Cetearyl Alcohol | 1.50 |
| Phenyl Trimethicone | 3.00 |
| Stearyl Heptanoate. Stearyl Caprylate | 3.00 |
| Dimethicone | 1.00 |
| Xanthan Gum | 0.20 |
| Isoamyl p-Methoxycinnamate | 5.00 |
| Water | Ad 100 |
| Methylpropanediol | 3.00 |
| Perfume oil P1. P2. P3 or P4 | 0.30 |
| Diazolidinyl urea | 0.10 |
| Substance of formula (I) | 0.50 |

TABLE XXXXVIII

Microemulsion gel (Amounts in % b.w.)

| Ingredient | Amount |
|---|---|
| Glycerol isostearate | 1.80 |
| Octoxyglycerol | 1.00 |
| Ceteareth-15 | 5.20 |
| PEG-150 Distearate | 1.00 |
| Aluminium chlorohydrate | 5.00 |
| Isotridecylisononanoate | 3.30 |
| Cyclomethicone | 6.60 |
| Perfume oil P1. P2. P3 or P4 | 0.70 |
| euxyl ® K145 (Methylchloroisothiazolinone. Methylisothiazlinone. Bronopol) | 0.10 |
| Substance of formula (I) | 0.40 |
| Water | Ad 100 |

TABLE XXXXIX

Air freshener in gel form (Amounts in % b.w.)

| Ingredient | Amount |
|---|---|
| Demineralised water | Ad 100 |
| Genugel ® X-6424 (carrageenan) | 2.00 |
| Arkopal ® N 100 or Tergitol ® NP 10 (Emulsifer) | 3.50 |
| Perfume oil P1. P2. P3 or P4 | 0.60 |
| Preventol ® D 7 (5-chloro-2-methyl-4-isothiazolin-3-one. 2-methyl-2H isothiazol-3-one) | 0.10 |
| Substance of formula (I) | 0.80 |

TABLE L

Cleaner. APC liquid. alkaline pH 8-10 (Amounts in % b.w.)

| Ingredients (INCI) | Amount |
| --- | --- |
| Aqua | 59.06 |
| Tri Sodium Citrate Dihydrate | 3.00 |
| Sodium Laureth Sulfate | 30.00 |
| Trideceth-9 | 5.00 |
| Ethanol | 2.00 |
| Citric Acid 10% solution | 0.24 |
| Perfume oil P1. P2. P3 or P4 | 0.50 |
| Mixture of 5-Chloro-2-methyl-2H-isothiazol-3-one and 2-Methyl-2H-isothiazol-3-one | 0.10 |
| Hydroxyacetophenone | 0.30 |

TABLE LI

Fabric softener (Amounts in % b.w.)

| Ingredients (INCI) | Amount |
| --- | --- |
| Aqua | 72.10 |
| Dialkylester ammomium methosulfate | 16.60 |
| Polydimethylsiloxane | 0.30 |
| Magnesiumchloride | 10.00 |
| Perfume oil P1. P2. P3 or P4 | 0.60 |
| Mixture of 5-Chloro-2-methyl-2H-isothiazol-3-one and 2-Methyl-2H-isothiazol-3-one | 0.10 |
| Hydroxyacetophenone | 0.40 |

TABLE LII

Liquid detergent (Amounts in % b.w.)

| Ingredients | Amount |
| --- | --- |
| Deionized water | 39.60 |
| Optical brightener | 0.10 |
| Coconut fatty acids (C12-C18) | 7.50 |
| Potassium hydroxide 50% solution | 4.30 |
| Propane-1.2-diol | 5.00 |
| Fatty alcohols C12-C15. 8 EO | 12.00 |
| Na-salt of secondary alkyl sulfonates (C13-C17) | 17.00 |
| Triethanolamine | 2.00 |
| Trisodium citrate dihydrate | 5.00 |
| Dequest 2066 Diethylenetriamine penta(methylene phosphonic acid) | 3.00 |
| Ethanol | 3.00 |
| Enzymes | 0.70 |
| Perfume oil P1. P2. P3 or P4 | 0.50 |
| Substance of formula (I) | 1.00 |

TABLE LIII

Liquid detergent concentrate (Amounts in % b.w.)

| Ingredients | Amount |
| --- | --- |
| Deionized water | 12.9 |
| Coconut fatty acids (C12-C18) | 10.0 |
| Fatty alcohols C12-C15. 8 EO | 26.0 |
| Na-salt of secondary alkyl sulfonates (C13-C17) | 26.5 |
| Triethanol amine | 8.5 |
| Na-salt of fatty alcohol sulfates C12-C14 | 3.0 |
| Ethanol | 5.5 |
| Urea | 4.5 |
| Enzymes | 0.9 |
| Citric acid | 1.0 |
| Perfume oil P1. P2. P3 or P4 | 0.7 |
| Substance of formula (I) | 0.8 |

TABLE LIV

Toilet cleaner (Amounts in % b.w.)

| Ingredients | Amount |
| --- | --- |
| Water | 93.0 |
| Kelzan ASX-T | 0.5 |
| Parafin sulfonate. sodium salt | 1.0 |
| Citric acid | 5.0 |
| Colorant (FD & C Yellow No. 6) | 0.1 |
| Perfume oil P1. P2. P3 or P4 | 0.3 |
| Preservative (Benzisothiazolinone. Glutaral) | 0.05 |
| Substance of formula (I) | 0.6 |

TABLE LV

Dish washing concentrate (Amounts in % b.w.)

| Ingredients | Amount |
| --- | --- |
| Sodium laurylsulfate | 31.0 |
| Propane-1.2-diole | 6.0 |
| Ethyl alcohol 96% | 7.0 |
| Palm tree glucosides | 6.0 |
| Coco betaine | 18.0 |
| Perfume oil P1. P2. P3 or P4 | 0.4 |
| Substance of formula (I) | 0.5 |
| Water | 31.6 |

TABLE LVI

Dish washing concentrate (Amounts in % b.w.)

| Ingredients | Amount |
| --- | --- |
| Palm tree glucosides | 4.0 |
| Sodium lauryl sulfate | 45.0 |
| Coco betaine | 8.0 |
| Ethyl alcohol 96% | 1.0 |
| Colorant (C.I. Pigment Blue 15) | 0.05 |
| Perfume oil P1. P2. P3 or P4 | 0.2 |
| Substance of formula (I) | 0.7 |
| Water | Ad 100 |

TABLE LVII

Solution for wet wipes (Amounts in % b.w.)

| Ingredients | INCI | Amount |
| --- | --- | --- |
| SymSol ® PF-3 | Water (Aqua). Pentylene Glycol. Sodium Lauryl Sulfoacetate. SodiumOleoyl Sarcosinate. Sodium Chloride. Disodium Sulfoacetate. SodiumOleate. Sodium Sulfate | 2.00 |
| Dragosantol ® 100 | Bisabolol | 0.10 |
| Glycerol 99.5 P. | Glycerol | 5.00 |
| Water | Water (Aqua) | Ad 100 |
| Hydrolite ® 5 | Pentylene Glycol | 5.00 |
| D-Panthenol 75 W | Panthenol | 0.80 |
| DragoCalm ® | Water (Aqua). Glycerol. *Avena Sativa* (Oat) Kernel Extract | 1.00 |
| Witch Hazel-Distillate | *Hamamelis Virginiana* (Witch Hazel) Water. Water (Aqua). Alcohol | 1.00 |
| Allplant Essence ® Org. Rose Geranium P | *Pelargonium Graveolens* Flower/Leaf/Stem Water | 1.00 |
| Perfume oil P1. P2. P3 or P4 | Parfum | 0.10 |
| Preservative | Phenoxyethanol | 0.30 |
| 4-hydroxyacetophenone | Hydroxyacetophenone | 0.50 |

Wet Cleansing Wipes

Preparation of a composition or mixture for neutralising unpleasant odours and/or desinfecting with wet cleansing wipes: The following components are mixed to form a composition or mixture: 30 parts by weight of dipropylene glycol, 25 parts by weight of Substance of formula (I), 15 parts by weight of isopropyl myristate, 15 parts by weight of triethyl citrate and 15 parts by weight of benzyl benzoate. Using an emulsifier (Dracorin GOC) a 0.05% aqueous solution is produced from this composition and is used to manufacture wet cleansing wipes.

TABLE LVIIIA

Peppermint Flavour PF1 (Amounts in % b.w.)

| Ingredients | Amount |
| --- | --- |
| Substance of formula (I) | Add 1000 |
| Isobutyraldehyde | 0.5 |
| 3-Octanol | 0.5 |
| Dimethyl sulphide | 0.5 |
| trans-2-Hexenal | 1.0 |
| cis-3-Hexenol | 1.0 |
| 4-Terpineol. natural | 1.0 |
| Isopulegol | 1.0 |
| Piperitone. natural. from eucalyptus | 2.0 |
| Linalool | 3.0 |
| 8-Ocimenyl acetate. 10% in triacetin | 5.0 |
| Isoamyl alcohol | 10.0 |
| Isovaleraldehyde | 10.0 |
| alpha-Pinene. natural | 25.0 |
| beta-Pinene. natural | 25.0 |
| Neomenthol. racemic | 40.0 |
| Eucalyptol (1.8-cineol). natural | 50.0 |
| L-Menthyl acetate of the formula D | 70.0 |
| L-Menthone | 220.0 |
| D-Isomenthone | 50.0 |
| L-Menthol | 483.5 |
| Nonenolide | 1.0 |

TABLE LVIIIB

Wintergreen flavor PF2 (Amounts in % b.w.)

| Ingredients | Amount |
| --- | --- |
| Substance of formula (I) | 8 |
| Anethole | 9 |
| I-menthol (natural or synthetic) | 45 |

TABLE LVIIIB-continued

Wintergreen flavor PF2 (Amounts in % b.w.)

| Ingredients | Amount |
| --- | --- |
| Peppermint oil *piperita* type | 2 |
| Peppermint oil *arvensis* type | 3 |
| Spearmint oil *spicata* type | 1 |
| Eugenol | 7 |
| Eucalyptol | 5 |
| Methyl salicylate | 20 |

TABLE LVIIIC

Isoamylacetate type flavor PF3 (Amounts in % b.w.)

| Ingredients | Amount I | Amount II |
| --- | --- | --- |
| Substance of formula (I) | 4 | 5 |
| Isoamylacetate | 2 | 2 |
| Ethylbutyrate | 0.5 | — |
| Butylbutyrate | — | 0.5 |
| Ethyl vanillin | 2 | — |
| Vanillin | — | 1 |
| Frambinon TM [4-(4-hydroxyphenyl)-2-butanon] | 0.5 | 0.5 |
| I-menthol | 8 | 11 |
| Triacetin | | 80 |
| 1.2-propylene glycol | 83 | |

TABLE LVIIID

Cinnamon type cool flavor PF4 (Amounts in % b.w.)

| Ingredients | Amount |
| --- | --- |
| Substance of formula (I) | 3 |
| Menthlymethylether | 3 |
| Cinnamaldehyde | 10 |
| Anethole | 9 |
| Eugenol | 2 |
| I-menthol | 40 |
| Peppermint oil *piperita* type | 10 |
| Peppermint oil *arvensis* type | 10 |
| Spearmint oil *spicata* type | 8 |
| (1R.2S.5R)-N-ethyl-2-isopropyl-5-methylcyclohexanecarboxamide (WS-3) | 2 |

TABLE LVIIID-continued

Cinnamon type cool flavor PF4 (Amounts in % b.w.)

| Ingredients | Amount |
|---|---|
| (1R.2S.5R)-N-[4-cyanomethylphenyl]-2-isopropyl-5-methylcyclohexane-carboxamide | 0.5 |
| Menthone glycerol ketal (Frescolat MGA ®) | 1.5 |
| Menthol propylene glycol carbonate (Frescolat MPC ®) | 1.5 |

TABLE LIX

Toothpaste (Amounts in % b.w.)

| Ingredients | Amount |
|---|---|
| Water (deionized) | Ad 100 |
| Sorbitol 70% | 45.00 |
| Trisodiumphosphate | 0.10 |
| Saccharin | 0.20 |
| Sodiummonofluorophosphate | 1.14 |
| PEG 1500 | 5.00 |
| Sident 9 (abrasive silica) | 10.00 |
| Sident 22 S (Thickening silica) | 8.00 |
| Sodiumcarboxymethylcellulose | 1.10 |
| Titanium (IV) oxide | 0.50 |
| Water (deionized) | 4.50 |
| Sodiumlaurylsulfate (SLS) | 1.50 |
| Flavour (PF1. PF2. PF3 or PF4) | 1.00 |
| Solbrol M (Sodium salt) (Methylparaben) | 0.15 |
| Hydroxyacetophenone | 0.40 |

TABLE LX

Toothpaste with zinc citrate (Amounts in % b.w.)

| Ingredients | Amount |
|---|---|
| Water (deionized) | Ad 100 |
| Sorbitol 70% | 45.00 |
| Trisodiumphosphate | 0.10 |
| Saccharin | 0.20 |
| Sodiummonofluorophosphate | 1.14 |
| PEG 1500 | 5.00 |
| Sident 9 (abrasive silica) | 10.00 |
| Sident 22 S (Thickening silica) | 8.00 |
| Sodiumcarboxymethylcellulose | 1.10 |
| Zinc citrate | 1.00 |
| Titanium (IV) oxide | 0.50 |
| Water (deionized) | 4.50 |
| Sodiumlaurylsulfate (SLS) | 1.50 |
| Flavour (PF1. PF2. PF3 or PF4) | 1.00 |
| SymDiol ® 68 (1.2-Hexanediol. Caprylylglycol) | 0.25 |
| Hydroxyacetophenone | 0.10 |

TABLE LXI

Mouth rinse (Amounts in % b.w.)

| Ingredients | Amount |
|---|---|
| Ethylalcohol | 10.00 |
| Cremophor CO 40 (PEG 40 hydrogenated castor oil) | 1.00 |
| Flavour (PF1. PF2. PF3 or PF4) | 0.25 |
| Water (deionized) | To 100.00 |
| Sorbitol 70% | 5.00 |
| Sodiumsaccharin 450 | 0.07 |
| Sodiumfluoride | 0.18 |
| Benzoic acid | 0.12 |
| Hydroxyacetophenone | 0.30 |

TABLE LXII

Gel dental cream (Amounts in % b.w.)

| Ingredients | Amount |
|---|---|
| Na carboxymethylcellulose | 0.40 |
| Sorbitol 70%. in water | 72.00 |
| Polyethylene glycol (PEG) 1500 | 3.00 |
| Na saccharinate | 0.07 |
| Na fluoride | 0.24 |
| Flavor (PF1. PF2. PF3 or PF4) | 1.00 |
| Abrasive silica | 11.00 |
| Thickening silica | 6.00 |
| Sodium dodecyl sulfate (SDS) | 1.40 |
| Dist. water | Ad 100 |
| p-Hydroxybenzoic acid (PHB) ethyl ester | 0.15 |
| 4-hydroxyacetophenone | 0.20 |

TABLE LXIII

Dental cream against plaque (Amounts in % b.w.)

| Ingredients | Amount |
|---|---|
| Carrageenan | 0.90 |
| Glycerol | 15.00 |
| Sorbitol 70%. in water | 25.00 |
| PEG 1000 | 3.00 |
| Na fluoride | 0.24 |
| Tetrapotassium diphosphate | 4.50 |
| Tetrasodium diphosphate | 1.50 |
| Na saccharinate | 0.40 |
| Precipitated silica | 20.00 |
| Titanium dioxide | 1.00 |
| Triclosan | 0.30 |
| Spearmint flavor (comprising 60 wt. % I-carvone and 25 wt. % I-menthol) | 1.00 |
| Sodium dodecyl sulfate | 1.30 |
| Dist. water | Ad 100 |
| Benzylalcohol | 0.50 |
| 4-hydroxyacetophenone | 0.25 |

TABLE LXIV

Dental cream for sensitive teeth (Amounts in % b.w.)

| Ingredients | Amount |
|---|---|
| Na carboxymethylcellulose | 0.70 |
| Xanthan gum | 0.50 |
| Glycerol | 15.00 |
| Sorbitol 70%. in water | 12.00 |
| Potassium nitrate | 5.00 |
| Sodium monofluorophosphate | 0.80 |
| Na saccharinate | 0.20 |
| Flavor (PF1. PF2. PF3 or PF4) | 1.00 |
| Ca-carbonate | 35.00 |
| Silicon dioxide | 1.00 |
| Sodium dodecyl sulfate (SDS) | 1.50 |
| Dist. water | Ad 100 |
| PHB methyl ester and PHB propyl ester | 0.20 |
| Substance of formula (I) | 0.50 |

TABLE LXV

Tooth cream and mouthwash 2-in-1 product (Amounts in % b.w.)

| Ingredients | Amount |
|---|---|
| Sorbitol | 40.00 |
| Glycerol | 20.00 |
| Ethanol | 5.00 |
| Water | Ad 100 |
| Na monofluorophosphate | 0.75 |

TABLE LXV-continued

Tooth cream and mouthwash 2-in-1 product (Amounts in % b.w.)

| Ingredients | Amount |
| --- | --- |
| Saccharin | 0.20 |
| Sident 9 (abrasive silicon dioxide) | 20.00 |
| Sident 22 S (thickening silicon dioxide) | 2.00 |
| Sodium carboxymethylcellulose | 0.30 |
| Sodium lauryl sulfate (SDS) | 1.20 |
| Color (Suspension. 1% in water) C.I. Pigment Blue 15 | 0.50 |
| Flavor (PF1. PF2. PF3 or PF4) | 0.90 |
| Solbrol M. sodium salt (methylparaben. sodium salt) | 0.20 |
| Substance of formula (I) | 0.30 |

TABLE LXVI

Ready-to-use mouthwash with fluoride (Amounts in % b.w.)

| Ingredients | Amount |
| --- | --- |
| Ethanol | 7.00 |
| Glycerol | 12.00 |
| Na fluoride | 0.05 |
| Pluronic F-127 ® (BASF. surface-active substance) | 1.40 |
| Na phosphate buffer pH 7.0 | 1.10 |
| Na saccharinate | 0.10 |
| Flavour (PF1. PF2. PF3 or PF4) | 0.15 |
| Chlorhexidine digluconate | 0.2 |
| Dist. water | to 100 |
| Sorbic acid | 0.20 |
| Substance of formula (I) | 0.30 |

TABLE LXVII

Sugar-free chewing gum (Amounts in % b.w.)

| Ingredients | Amount |
| --- | --- |
| Chewing gum base | 30.00 |
| Sorbitol. powder | Ad 100 |
| Palatinite | 9.50 |
| Xylitol | 2.00 |
| Mannitol | 3.00 |
| Aspartame | 0.10 |
| Acesulfame K | 0.10 |
| Emulgum/emulsifier | 0.30 |
| Sorbitol 70%. in water | 14.00 |
| Glycerol | 1.00 |
| Flavor (PF1. PF2. PF3 or PF4 | 1.50 |
| Substance of formula (I) | 0.20 |

What claimed is:

1. An antimicrobial composition consisting of
(a) 4-hydroxyacetophenone
and
(b) one second antimicrobial agent selected from the group consisting of 2-phenylethyl alcohol, 3-phenyl propanol, benzyl alcohol, 1,3 propandiol, 3-heptoyl-2,2-propandiol, 1, 2-pentanediol, 1,2-hexandiol, 1,2 octandiol, 2-phenoxyethanol, 3-hexoxy-propan-1,2-diol, 3-heptoxy-propan-1,2-diol, 3-octoxy-propan-1,2-diol, ethylhexyl glycerin, 3-benzyloxy-propan-1,2-diol, wherein component (b) is present in an amount of from 1 to about 25 weight percent based upon the total weight of the antimicrobial composition.

2. The composition of claim 1 wherein the second antimicrobial agent is present in an amount of from 2 to 20 weight percent based on the total weight of the composition.

3. The composition of claim 1 wherein the second antimicrobial agent is present in an amount of from 5 to 10 weight percent based on the total weight of the composition.

4. The composition of claim 3 wherein the second antimicrobial agent is selected from the group consisting of 2-phenylethyl alcohol, 3-phenyl propanol, benzyl alcohol, 1,2-pentanediol, 1,2-hexandiol, 1,2-octanediol, 2-phenoxyethanol, and ethylhexyl glycerin.

5. An antimicrobial composition consisting of
(a) 4-hydroxyacetophenone, and
(b) one second antimicrobial agent selected from the group consisting of 2-phenylethyl alcohol, 3-phenyl propanol, benzyl alcohol, 1,2-pentanediol, 1,2-hexanediol, 1,2-octanediol, 2-phenoxyethanol and ethylhexyl glycerin wherein component (b) is present in an amount of from 1 to about 25 weight percent based upon the total weight of the antimicrobial composition.

* * * * *